US012653906B2

(12) United States Patent (10) Patent No.: US 12,653,906 B2
Gordon et al. (45) Date of Patent: Jun. 16, 2026

(54) DAMAGE-TARGETED TREATMENTS OF DISEASE

(71) Applicant: DELTA NEXT-GENE, LLC, Santa Monica, CA (US)

(72) Inventors: Erlinda M. Gordon, Santa Monica, CA (US); Frederick L. Hall, Carmel Valley, CA (US)

( * ) Notice: Subject to any disclaimer, the term of this patent is extended or adjusted under 35 U.S.C. 154(b) by 683 days.

(21) Appl. No.: 17/976,164

(22) Filed: Oct. 28, 2022

(65) Prior Publication Data

US 2023/0080185 A1 Mar. 16, 2023

Related U.S. Application Data

(63) Continuation of application No. PCT/US2021/030282, filed on Apr. 30, 2021.

(51) Int. Cl.
| | |
|---|---|
| *C07H 21/04* | (2006.01) |
| *A61K 39/395* | (2006.01) |
| *A61K 45/06* | (2006.01) |
| *A61K 48/00* | (2006.01) |
| *A61P 11/00* | (2006.01) |
| *A61P 31/14* | (2006.01) |
| *A61P 37/06* | (2006.01) |

(52) U.S. Cl.
CPC .... *A61K 48/0025* (2013.01); *A61K 39/39533* (2013.01); *A61K 45/06* (2013.01); *A61P 11/00* (2018.01); *A61P 31/14* (2018.01); *A61P 37/06* (2018.01)

(58) Field of Classification Search
CPC ...................................................... C12N 15/86
See application file for complete search history.

(56) References Cited

U.S. PATENT DOCUMENTS

2012/0027727 A1* 2/2012 Hall ........................ A61P 43/00
424/93.2

FOREIGN PATENT DOCUMENTS

WO WO-2017087610 A1 * 5/2017 ........... C07D 405/12

OTHER PUBLICATIONS

Cao et al. (Nature Reviews, Immunology, 20, May 2020, 269-270).*
Adriaansen et al. (Rheumatology 2006;45:656-668).*
Bessis et al. (Joint Bone Spine 73 (2006) 169-176).*
Lambert et al. (University of New Mexico, UNM Digital Repository, May 7, 2020, pp. 1-10).*

* cited by examiner

*Primary Examiner* — Amy Rose Hudson
(74) *Attorney, Agent, or Firm* — Hartmans Law Corporation; Joel Fogelson

(57) ABSTRACT

Methods of treating viral infectious diseases such as coronavirus disease 2019 and other diseases causing organ damage in a subject are provided.
Treatments include administration of a targeted retrovector to the subject. Among the effects of these treatments is the lessening or prevention of complications of the disease, particularly those arising from pathogenic immune responses.

1 Claim, 22 Drawing Sheets

A  Phase Contrast

B  Apoptosis Detection

A Mx-null    B CAE-nBg    C Mx-nBg

Preoperative dnG1    Preoperative aG1    Preoperative null

4th week Postoperative dnG1    4th week Postoperative aG1    4th week Postoperative null

DAMAGE-TARGETED TREATMENTS OF DISEASE

RELATED APPLICATIONS

This application is a continuation of International Patent Application No. PCT/US2021/030282, filed on Apr. 30, 2021, entitled "DAMAGE-TARGETED TREATMENTS OF DISEASE," which in turn claims priority to U.S. Provisional Patent Application No. 63/018,298, filed on Apr. 30, 2020, entitled "METHODS FOR TREATING DISEASES AND DISORDERS," and U.S. Provisional Patent Application No. 63/078,159, filed on Sep. 14, 2020, entitled "DAMAGE-TARGETED TREATMENTS OF DISEASE," each of which is hereby incorporated herein by reference in its entirety.

TECHNICAL FIELD

The present disclosure relates generally to methods of treating disease using targeted therapies.

BACKGROUND

Coronavirus disease 2019 (COVID-19) is an infectious disease caused by severe acute respiratory syndrome coronavirus 2 (SARS-CoV-2). COVID-19 causes life threatening complications known as cytokine storm and Acute Respiratory Distress Syndrome (ARDS). These complications are the main causes of death in this global pandemic. The inventors propose a solution to this urgent unmet medical need.

DETAILED DESCRIPTION

Figure 1:
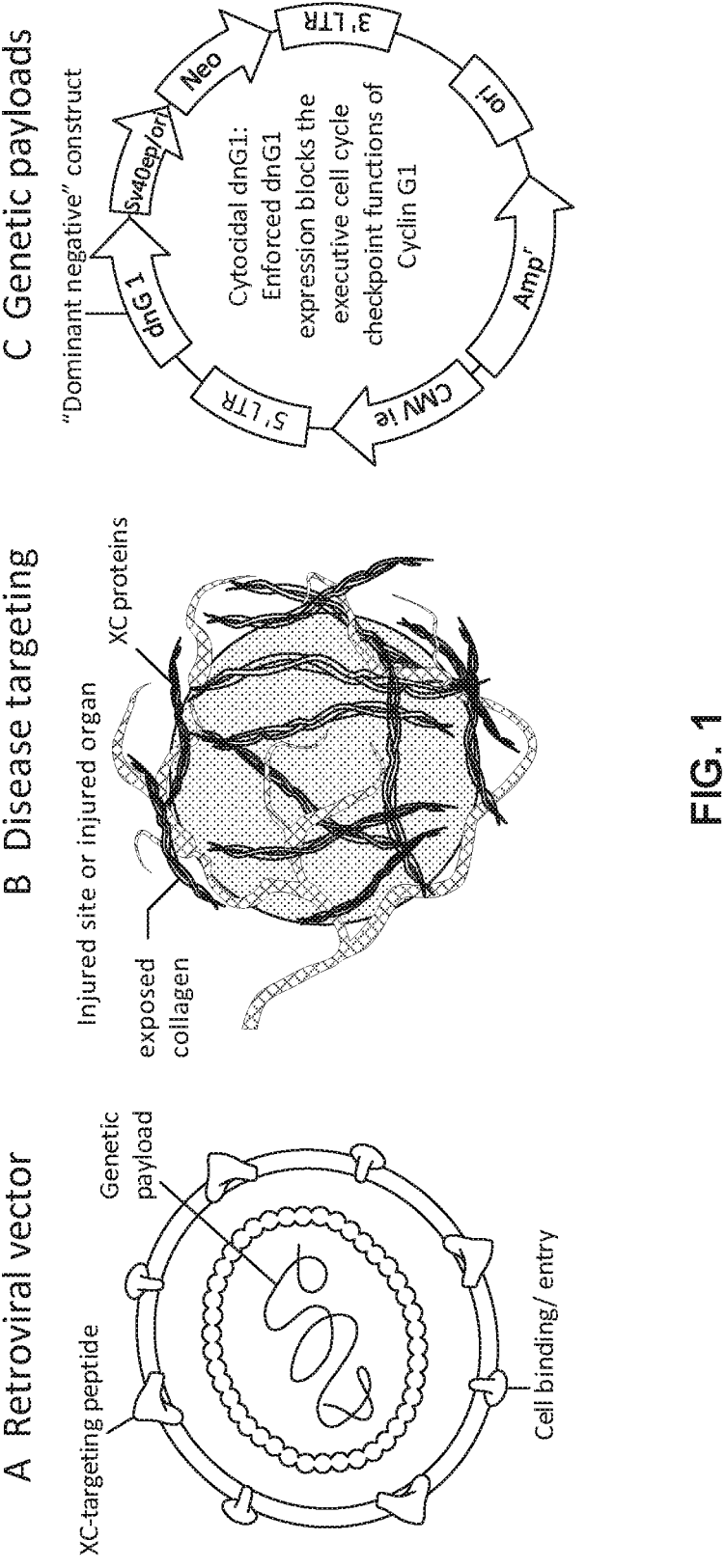
FIG. 1 is an illustration representing the DeltaRex-G vector. The DeltaRex-G vector displays an XC targeting peptide (panel A), for binding to exposed collagenous (XC) proteins in the diseased lung environment (DLE) (panel B), and encodes a dominant negative targeted retrovector gene (panel C).

The present disclosure is directed to methods and therapeutics for treating viral infectious diseases, particularly diseases that cause damage to affected tissues or organs and which produce proliferative immune cell responses. COVID-19 is discussed as a particular example of such a disease in which such responses can give rise to serious complications. However, it will be understood that the present disclosure also encompasses treatment of other such infectious diseases, as well as other diseases that involve pathogenic immune responses, such as autoimmune diseases.

One challenge to a complete understanding of COVID-19 is the question of whether adaptive immune responses to SARS-CoV-2 are protective, pathogenic, or both, depending on the timing, nature, or magnitude of the adaptive immune response. While it appears likely that an early T cell response against SARS-CoV-2 is protective, late T cell responses may instead amplify pathogenic inflammatory outcomes in the presence of sustained high viral loads in the lungs or other affected organs. Critical and fatal COVID-19 outcomes are associated with elevated levels of inflammatory cytokines and chemokines, including interleukin-6 (IL-6), interleukin-8 (IL-8), interleukin-1-beta (IL-1β), and tumor necrosis factor alpha (TNF-α).

Infiltration of large numbers of inflammatory cells have been observed in the lungs of severe COVID-19 patients which presumably consist of a constellation of innate immune cells and adaptive immune cells. The majority of infiltrating innate immune cells are neutrophils, which can actually induce lung injury. The majority of infiltrating adaptive immune cells are CD8+ T cells, as indicated by a significant reduction observed in circulating T cells. While these cytotoxic T cells can kill viruses, they also contribute to lung injury. Circulating monocytes respond to the cytokine GM-CSF released by these pathological T cells. CD14+ CD16+ inflammatory monocyte subsets, which seldom exist in healthy subjects, have also been observed at significantly higher percentages in COVID-19 patients. These inflammatory CD14+ CD16+ monocytes exhibit high expression of IL-6, which likely accelerate the progression of a systemic inflammatory response.

SARS-CoV-2 infection often gives rise to life threatening complications including cytokine response syndrome (CRS), an excessive upregulation of proinflammatory cytokines; rapid onset cases of CRS are often referred to as a "cytokine storm." Symptoms of CRS include raging fevers, headaches, intense fatigue, muscle aches, and loss of taste and smell. Another frequent complication of COVID-19 is ARDS, which manifests as difficulty breathing and can progress to pneumonia and eventually further to respiratory failure. ARDS can manifest levels of severity, which can be defined based on the degree of hypoxemia calculated as the ratio of arterial oxygen tension to the fraction of inspired oxygen ($PaO_2/FiO_2$). According to one such definition (known as the Berlin definition), a measurement of 200-300 mm Hg indicates mild ARDS, 100-199 mm Hg indicates moderate ARDS, and <100 mm Hg indicates severe ARDS. These complications are believed to be caused not just by the virus itself, but by an exaggerated immune reaction to the infection. The overactive immune cells are thought to make certain proinflammatory chemicals (cytokines) that cause raging fevers and damage to the lungs, liver, kidneys, heart, brain and other organs.

Figure 22A:
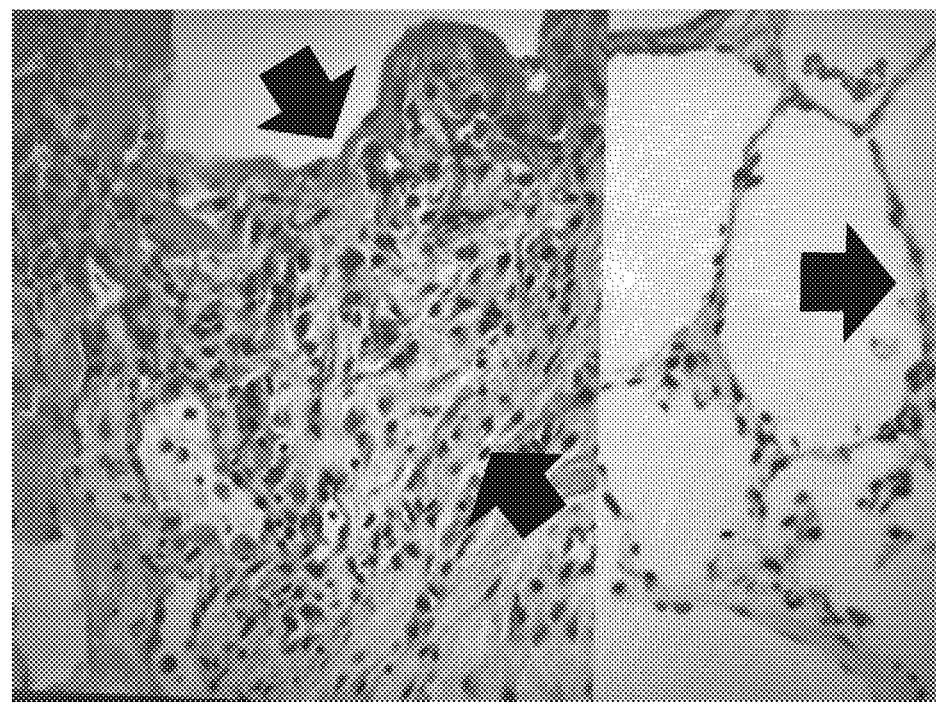
FIG. 22A are histopathology images representing damaged lung tissue in acute respiratory distress syndrome of COVID-19 (left panel) and normal lung tissue (right panel).
Figure 22B:
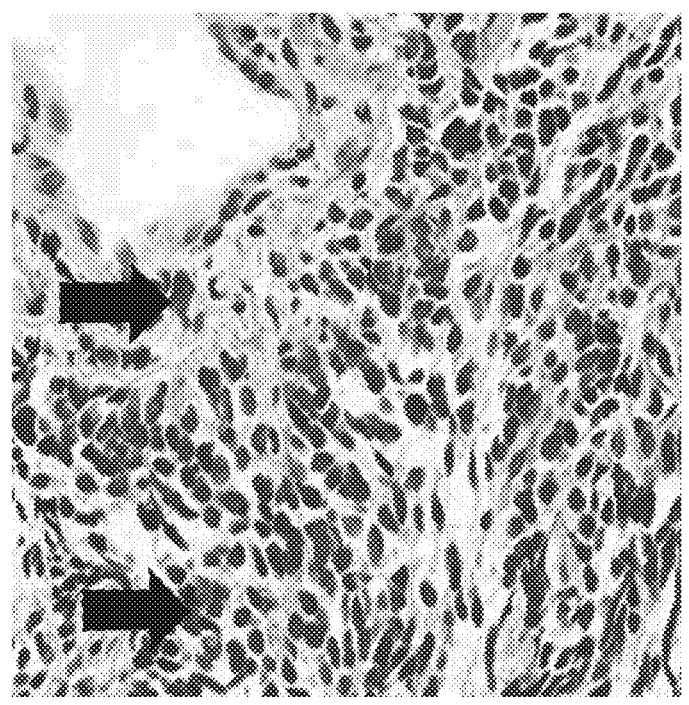
FIG. 22B is a histopathology image representing a tumor microenvironment in lung cancer of cancer metastatic to lung.

The inventors have observed that COVID-19 patients share common symptomatology, histopathologic and hematologic features with patients having late stage metastatic cancers. Destruction of lung tissue by invading immune cells exposing collagenous (XC) proteins and interstitial mononuclear inflammatory infiltrates dominated by activated lymphocytes, majorly CD8+ T cells, can be observed (FIG. 22A). Similarly, in lung cancer tissues, destruction of lung tissue by invading tumor cells exposing collagenous (XC) proteins and infiltration of lung tissue by rapidly dividing or proliferative cancer cells can be observed by histopathology (FIG. 22B). It has further been found that these elements are susceptible to activity of certain therapeutic agents in such a way that reduces or arrests these pathogenic responses. Consequently, the inventors have recognized that such therapeutic agents can be used in a treatment to lessen or prevent severe complications arising from COVID-19 and other such infectious diseases, thereby increasing survivability and improving recovery outcomes.

Some key commonalities in symptomatology, histopathology and hematology between metastatic cancers and COVID-19 are as follows, though this list is not necessarily exhaustive:

1. Exposed collagenous proteins are an indicator of tissue damage in some tissue types. Abnormally exposed collagenous XC proteins are found in the tumor microenvironment (TME) of invading tumors. These XC proteins are also found in the damaged lung environment (DLE) of COVID-19 related acute respiratory distress syndrome (ARDS).

2. One of the body's immune responses to neoplasm growth is the migration of various immune cells to the tumor tissue. These tumor infiltrating lymphocytes are commonly found in the tumor microenvironment of advanced Stage 4 cancer. Infiltrating lymphocytes are similarly found in the damaged lung environment of COVID-19 patients.

3. Tumor lysis syndrome is a serious condition that can occur in cancer patients as a result of rapid tumor cell breakdown (often due to cancer therapy) and the consequent release of massive amounts of intracellular contents as well as cytokines. Cytokine storm often occurs from tumor lysis syndrome in leukemias and, as discussed above, as part of the exaggerated immune response in COVID-19.

4. There is a frequent incidence of fever, intense fatigue, myalgia, deep vein thrombosis, disseminated intravascular coagulation, stroke, and abnormal coagulation in both advanced Stage 4 cancer and COVID-19.

5. Abnormalities such as increased serum levels of acute phase reactants, ferritin, C-reactive protein, lactate dehydrogenase, neutropenia, thrombocytopenia, lymphopenia, disseminated intravascular coagulation, and abnormal coagulation are frequently detected in laboratory analysis results of both advanced cancer and COVID-19 patients.

Generally speaking, it can be said that COVID-19 and metastatic cancers exhibit key commonalities in that they both involve tissue damage and proliferative immune cell responses. The inventors have found that methods of treating COVID-19 with improved outcomes can include administration of therapeutic agents that provide for targeted delivery to affected/injured tissues and have the ability to stem proliferative cell responses. More specifically, such a therapeutic agent can comprise a targeted retrovector encoding an anti-cyclin G1 construct as genetic payload. The term "targeted" as used herein refers to properties or features that cause a retrovector, upon systemic administration in a subject, to migrate to or concentrate in tissues that exhibit a particular environment or characteristic related to a disease state in the subject.

In some embodiments, a method of treating a viral infectious disease in a subject comprises administering an effective amount of a targeted retrovector to the subject. In some embodiments, the disease arises from infection of the subject by viruses including, but not limited to, human coronaviruses. In certain embodiments, the viral infectious disease is coronavirus disease 2019 (COVID-19), particularly moderate to severe COVID-19, and more particularly severe COVID-19. In other embodiments, a method of treating a disease that causes organ damage in a subject comprises administering an effective amount of a targeted retrovector to the subject. In a particular embodiment, the disease is an autoimmune disease including, but not limited to, rheumatoid arthritis, lupus erythematosus, atopic dermatitis, lichen planus, psoriasis, autoimmune hemolytic anemia, idiopathic thrombocytopenia, celiac disease, inflammatory bowel syndrome, ulcerative colitis, Crohn's disease, Sjogren's syndrome, scleroderma, multiple sclerosis, Parkinson's disease, polymyalgia rheumatica, Type 1 diabetes, alopecia areata, ankylosing spondylitis, vasculitis, temporal arteritis, and autoimmune myocarditis.

An unexpected aspect of the present disclosure is that an effective treatment for tissue damage in a subject arising from COVID-19 can comprise administering a targeted retrovector with a cytocidal gene payload. As discussed above, tissue damage in COVID-19 is caused by activated/proliferative immune cells, and it is believed that killing these immune cells will reduce or arrest such damage. In certain embodiments, the targeted retrovector is DeltaRex-G. DeltaRex-G (see FIG. 1) is a disease-seeking gene therapy encoding a designer killer gene, i.e. a cytocidal dominant negative human cyclin G1, as a payload. DeltaRex-G comprises an MLV-based nanoparticle (~100 nm) modified to include a collagen-binding motif and a vector payload encoding an N-terminal deletion mutant human CCNG1 construct under the control of a hybrid LTR/CMV promoter. The vector also contains the neomycin resistance (neo') gene which is driven by the SV40 early promoter. The DeltaRex-G vector can be produced by transient co-transfection of three plasmids in 293T (human kidney 293 cells transformed with SV40 large T antigen) producer cells obtained from a fully validated master cell bank.

When injected intravenously, the collagen binding motif of DeltaRex-G nanoparticles acts as a navigational system that targets XC proteins, thus increasing the effective drug concentration in the vicinity of the XC proteins. In the context of treatment of metastatic cancer, the inventors have shown that intravenously administered DeltaRex-G is targeted to XC proteins in the TME, thus increasing the effective drug concentration in the TME in the vicinity of proliferative cancer cells. The DeltaRex-G nanoparticles then enter the rapidly dividing cancer cells and kill them by arresting the G1 phase of the cell division cycle. The inventors have further found that, when injected intravenously to a subject infected with SARS-CoV-2, DeltaRex-G nanoparticles target XC proteins found in injured tissues (e.g. inflamed lung, kidney, liver), thus increasing the effective drug concentration at the site of injury, particularly in the vicinity of activated/proliferative T cells evoked by COVID-19. The DeltaRex-G nanoparticles then transduce the proliferative T cells and kill them by arresting the G1 phase of the cell division cycle, hence reducing cytokine release and the severity of ARDS. Intravenous DeltaRex-G has minimal systemic toxicity due to its navigational system (targeting properties) that limits the biodistribution of DeltaRex-G only to areas of injury where XC proteins are abnormally found.

While not seeking to be bound to any particular theory, it is contemplated that disease-seeking retrovectors of the present disclosure may exert therapeutic effects through mechanisms of action other than—or in addition to—those discussed above. For example, the non-pathogenic RNA virus-based retrovector may mimic the pathogenic RNA virus (e.g. SARS-CoV-2) by binding to viral receptors on human cells and prevent and prevent cell entry of the pathogenic virus by competitive inhibition. In another aspect, where the retrovector and the pathogenic virus bind to different receptors, the retrovector may prevent binding and entry of the pathogen by crowding or neutralization of the pathogen.

In certain embodiments, the targeted retrovector is administered intravenously. In other embodiments, the targeted retrovector may be administered using another route of administration, e.g., by subcutaneous, intramuscular, intradermal, transdermal, intrathecal, intracerebral, intraperitoneal, intranasal, epidural, pulmonary, intravitreal, or oral routes. Administration may be immediate or rapid, such as by injection, or carried out over a period of time, such as by infusion or administration of controlled or delayed release formulations.

In certain embodiments, a targeted retrovector encoding a cytocidal dominant negative cyclin G1 construct is administered at a therapeutically effective dose. A therapeutically effective dose for a given subject may be determined by an empiric dosing approach (e.g., a calculus of parity) based upon various measured or estimated parameters, such as by nonlimiting example, body weight, blood volume, target cell count, and desired multiplicity of infection. In some embodiments, the vector is administered at a dose of greater than about $1\times10^{11}$ colony forming units (cfu). As discussed below with respect to various embodiments, the vector may be also be introduced at a dose of greater than about $1\times10^{11}$ cfu or other suitable dose based on the particular parameters of the disease presentation in the individual and/or one or more selected clinical endpoints. In some embodiments, the dose is from about $1\times10^{11}$ cfu to about $4\times10^{11}$ cfu. In more particular embodiments, the dose is from about $1\times10^{11}$ cfu to about $3\times10^{11}$ cfu, or from about $2\times10^{11}$ cfu to about $4\times10^{11}$ cfu.

The targeted retrovector may be administered more than once to an individual in need thereof. In various embodiments, administration comprises administering an effective dose at a selected frequency for a selected period of time. In some embodiments, the retrovector may be administered at least two times per week. In some embodiments, the retrovector is administered at least three times per week. In some embodiments, the retrovector is administered to the subject daily for a period from about 3 days to about 21 days. In certain embodiments daily administration is performed for a period of from about 7 to about 14 days.

In some embodiments, the targeted retrovector is administered until a selected clinical endpoint is attained. Potentially relevant endpoints include a change in cytokine pattern, a reduction in viral load, a reduction in ARDS severity level, and lessening of one or more symptoms. Symptoms can include fever, increased respiratory rate, and lowered peripheral capillary oxygen saturation (SpO$_2$). In particular embodiments the change in cytokine pattern can comprise a reduction in the level of one or more cytokines. In various embodiments the cytokine includes one or more of IL-6, IL-8, IL-1β, and TNF-α. In various embodiments, the retrovector can be administered to the subject in conjunction with other therapeutic agents, for example as part of a combination therapy. In particular embodiments, the retrovector can be administered in combination with a chemotherapeutic agent or a monoclonal antibody.

The following example is illustrative of disclosed methods and compositions. In light of this disclosure, those of skill in the art will recognize that variations of the example and other examples of the disclosed methods would be possible without undue experimentation.

EXAMPLES

The following examples are for illustration only. In light of this disclosure, those of skill in the art will recognize that variations of these examples and other embodiments of the disclosed subject matter are enabled without undue experimentation.

Example 1—DeltaRex-G Retroviral Vector Construct and Characterization

Figure 2:
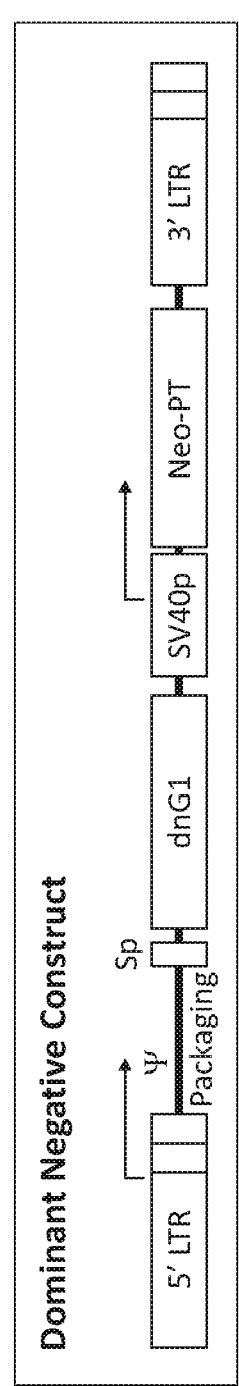
FIG. 2 is an illustration representing the DeltaRex-G vector with molecular genetic components.
Figure 2:
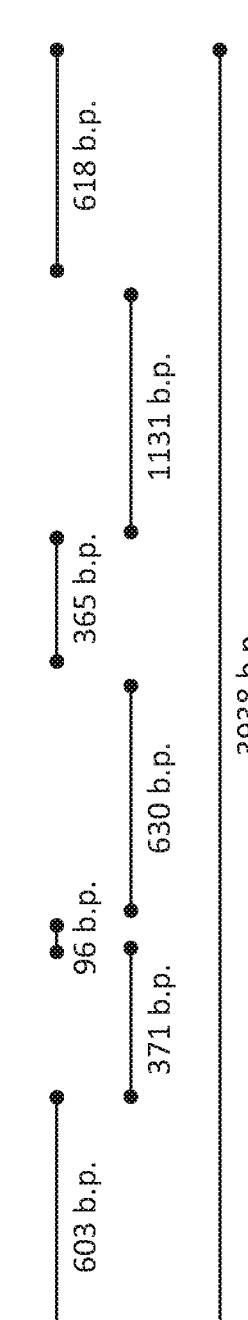

DeltaRex-G is a disease-targeted, MLV-based nanoparticle (~100 nm) encoding a N terminal deletion mutant human CCNG1 construct under the control of a hybrid LTR/CMV promoter (FIG. 2). The vector also contains the neomycin phosphotransferase resistance (Neo-PT) gene which is driven by the SV40 early promoter. The DeltaRex-G vector is produced by transient co-transfection of 3 plasmids in 293T (human kidney 293 cells transformed with SV40 large T antigen) producer cells obtained from a fully validated master cell bank.

Components of the transfection system include pC-GP/SvN (CMV driven MoMuLv gag-pol plasmid), pCMV-Mx-Env (Mx-targeted env expression plasmid), and pERV-dnG1/neo (dominant negative cyclin G1 retroviral vector plasmid).

The pC-GP/SvN plasmid encodes the MoMuLv gag-pol polyprotein driven by the CMV immediate-early promoter enhancer. The gag-pol ORF is flanked by 5' Gag UTR (273 bases), including the GlycoGag MLV IRES region; and by 3' Pol UTR (36 bases). The gag-pol coding sequence—originally flanked by EcoR I cloning sites—was derived from clone 3P0 as pGag-pol-gpt. In this new version of the plasmid, the 5' Eco RI cloning site is replaced by the introduction of Asc I and Sbf I restriction sites; and an Fse I site was added following the 3' Eco RI restriction site, which is retained. The vector backbone is pcDNA3.1+ (Invitrogen). Polyadenylation signal and transcription termination sequences from bovine growth hormone enhance RNA stability. An SV40 ori is featured along with the e.p. for episomal replication in cell lines that express SV40 large T antigen. Correct orientation was confirmed by restriction digestion with SalI and the insert was further characterized by digestion with EcoRI and HindIII. Both the 5' and 3' sequences of the gag-pol insert were confirmed by DNA sequence analysis utilizing the T7 promoter binding site primer (51) and the pcDNA3.1/BGH reverse priming site (AS1), respectively. The resulting plasmid, designated pCgpn, encodes the gag-pol polyprotein driven by the strong CMV promoter and a neomycin resistance gene driven by the SV40 early promoter. The presence of an SV40 on in this plasmid enables episomal replication in cell lines that express the SV40 large T antigen (i.e., 293T producer cells).

Enhanced CMV expression plasmid bearing Mx-Env, a targeted retroviral vector envelope construct: the amphotropic env (4070A) was modified by the addition of a unique Pst I restriction site near the N-terminus of the mature protein (CAE-P); engineered to exhibit an XC-binding motif (GHVGWREPSFMALSAA); and re-generated by PCR to eliminate all upstream (5') and downstream (3') retroviral sequences in this plasmid construct. The plasmid backbone (phCMV1) provides an optimized CMV prompter/enhancer/intron to drive the expression of env, in addition to an SV40 promotor/enhancer, which enables episomal replication in vector producer cells expressing the SV40 large T antigen (293T). Positive selection is provided by the kanamycin resistance gene. The expression of the chimeric envelope protein in 293T producer cells is driven by the strong CMV i.e. promoter. The chimeric envelope is processed correctly and incorporated stably into retroviral particles, which exhibit the gain-of-function phenotype without appreciable loss of infectious titer. Correct orientation of the collagen-binding domain was confirmed by DNA sequence analysis, and plasmid quality control was confirmed by restriction digestion Pst I, which linearizes the plasmid and releases the collagen-binding domain.pERV-dnG1/neo, a dominant negative cyclin G1 retroviral vector plasmid.

The pERV-dnG1/neo plasmid construct contains the deletion mutant of the human cyclin G1 gene, encoding a.a. 41 to 249 driven by the hybrid LTR promoter, packaging sequences, and the bacterial neomycin resistance gene under the control of an internal SV40 early promoter. The truncated cyclin G1 gene was initially cloned into a TA cloning vector (Invitrogen), followed by Not I/Sal I digestion and ligation of the purified insert into a Not I/Sal I digested pG1XSvNa retroviral expression vector (provided by Genetic Therapy, Inc., Gaithersburg, MD) to produce the pdnG1SvNa vector complete with 5' and 3' LTR sequences and a Ψ "packaging" sequence. An additional CMV promoter-enhancer (which is not packaged) was prepared by PCR from a CMV-driven pIRES template (Clontech), incorporating Sac II overhangs, and cloned into the unique Sac II site of pdnG1SvNa upstream of the 5'LTR to produce pdnG1/C-REX. Correct orientation and sequence of the CMV promoter was confirmed by restriction digestion and DNA sequence analysis, as was the dnG1 coding sequences. Plasmid identity and quality control is confirmed by digestion with Sac II (which releases the 750 bp CMV promoter) and Bgl II (which cuts at a unique site within the dnG1 construct). The resulting nanoparticles are replication-incompetent Type C retroviral particles of uniform diameter (~100 nm). The particles are harvested as a suspension in a solution of 95% final proprietary serum-free formulation medium and 1.2% human serum albumin.

Figure 3:
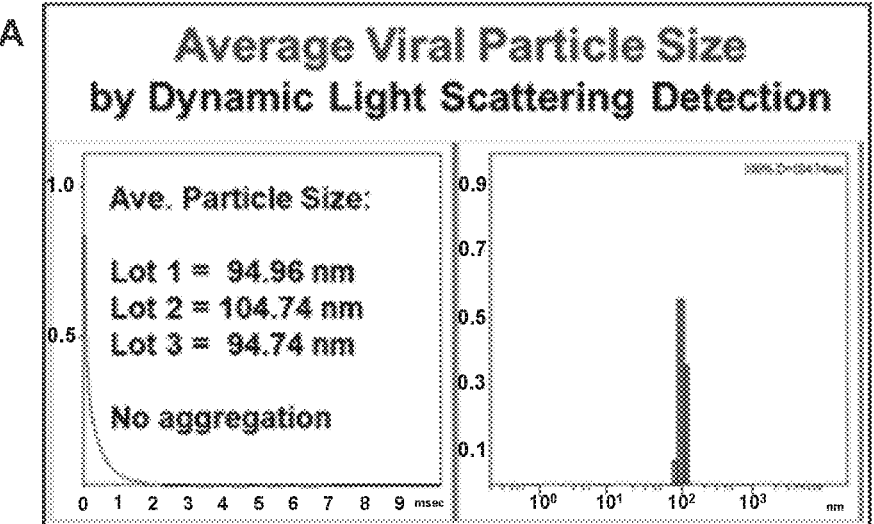
FIG. 3 shows graphical representations of DeltaRex-G characteristics. Average particle size and light scattering detection (panel A), an electronmicrograph (panel B), and a depiction of a collagen binding assay (panel C) are shown.
Figure 3:
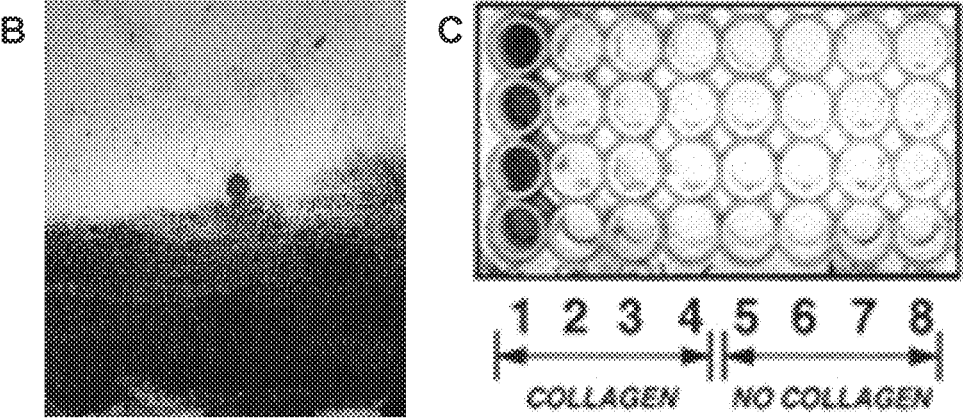

The characteristics of DeltaRex-G are shown in FIG. 3 panel A. The average size of clinical DeltaRex-G nanoparticle is ~100 nm by dynamic light scattering; (FIG. 3 panel B) An electronmicrograph shows a Delta Rex-G nanoparticle bound on top of Type 1 collagen in a collagen binding assay; (FIG. 3 panel C) The DeltaRex-G XC-targeted vector bound tightly to Type collagen (Lane 1) while non-targeted control vectors were washed away (Lanes 2-4), in a collagen binding assay. In the absence of collagen, both targeted and non-targeted vectors were washed away with phosphate buffered saline (PBS) in Lanes 5-8.

Example 2—In Vitro Studies in Human Osteosarcoma Cells

Figure 4A:
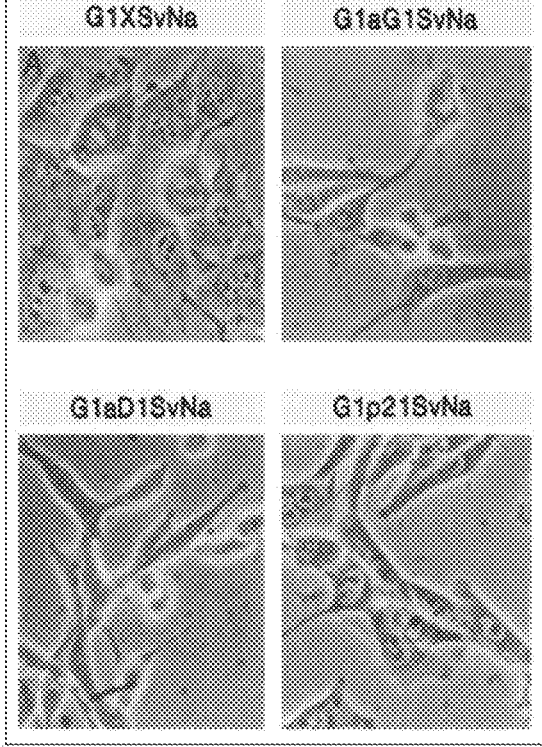
FIG. 4A shows phase contrast images of MG-63 human osteosarcoma cells 72 h after transduction with retroviral vectors bearing anti (as)-cyclin G1 (G1aG1SvNa) compared to as-cyclin G1 (G1aD1SvNa, p21 G1p21SvNa) or the control (G1XSvNa) vector.
Figure 4B:
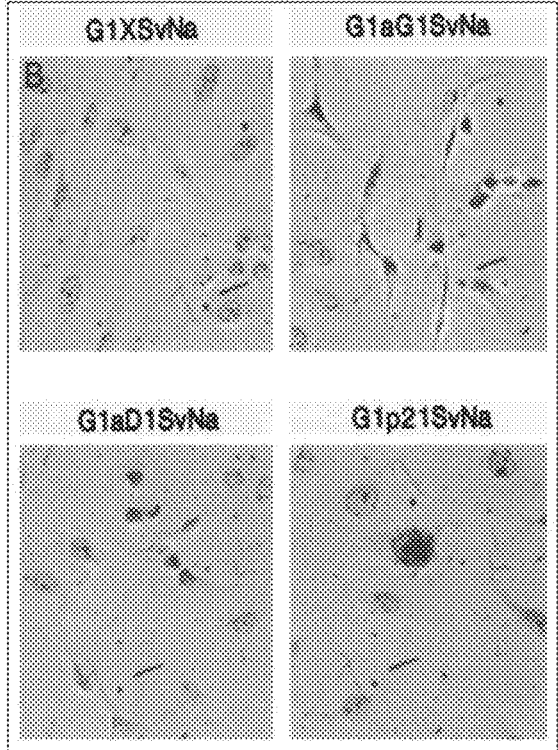
FIG. 4B is a microscopy image depicting apoptotic MG-63 cells by immunocytochemical staining of modified DNA fragments. Apoptotic cells are identified as cells with dark-staining nuclei.

The mechanism of action of cyclin G1 knock-out constructs was demonstrated using a non-targeted retroviral vector bearing an antisense (as) cyclin G1 gene. It has been shown that down-regulation of cyclin G1 protein expression using a retroviral vector bearing an as-cyclin G1 construct induced apoptosis of human MG-63 osteosarcoma cells. Osteosarcoma cell cultures transduced with the as-cyclin G1 (G1aG1SvNa) vector showed morphological evidence of apoptosis, including cell shrinkage, nuclear segmentation, chromatin condensation and nuclear fragmentation (FIG. 4A). A molecular and immuno-cytochemical approach was used to detect the endonuclease-mediated DNA cleavage fragments in transduced MG63 cell cultures to investigate the mechanism of cell death further (FIG. 4B). The induction of apoptosis in these cultures was determined to be highly significant in as-cyclin G1 vector-transduced cells (mean incidence 38.8±5%; n=6) when compared to cultures transduced with the control vector bearing only the neor gene (3.6±4.1%; n=6; p<0.001). Consistent with these findings, vectors bearing cell cycle control knock-out constructs, as-cyclin D1 (G1aD1SvNa) or p21 (G1p21SvNa) induced similar results.

Figure 5:
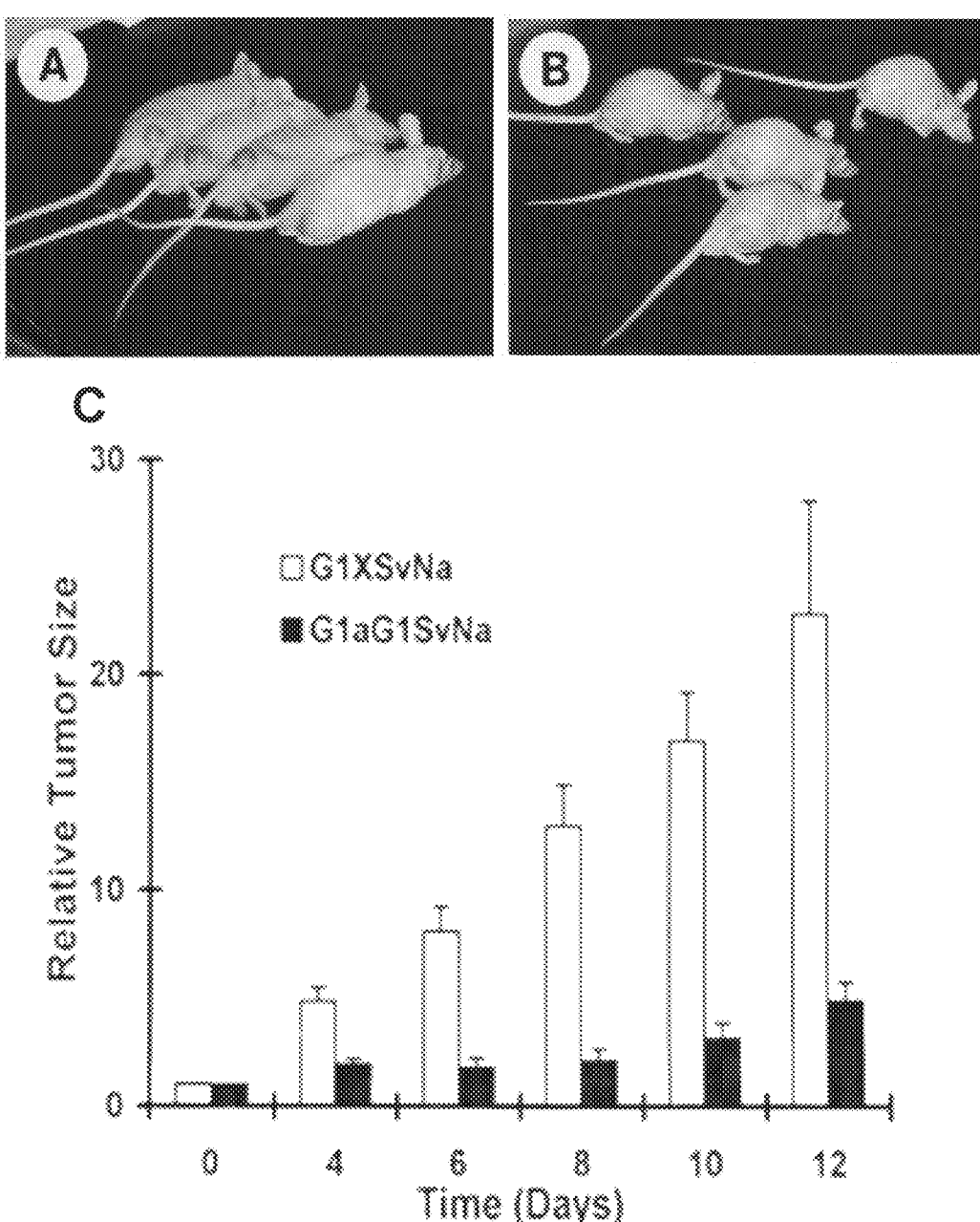
FIG. 5 shows in vivo effects of as-cyclin G1 vector in subcutaneous human MMNG/HOS osteosarcoma model in nude mice. Photographs of tumor-bearing mice that are control vector-treated (panel A) and as-cyclin G1 vector-treated (panel B) are shown. Panel C is a graphical representation of relative tumor size of tumor-bearing mice treated with the control vector or the as-cyclin G1 vector.
Figure 6:
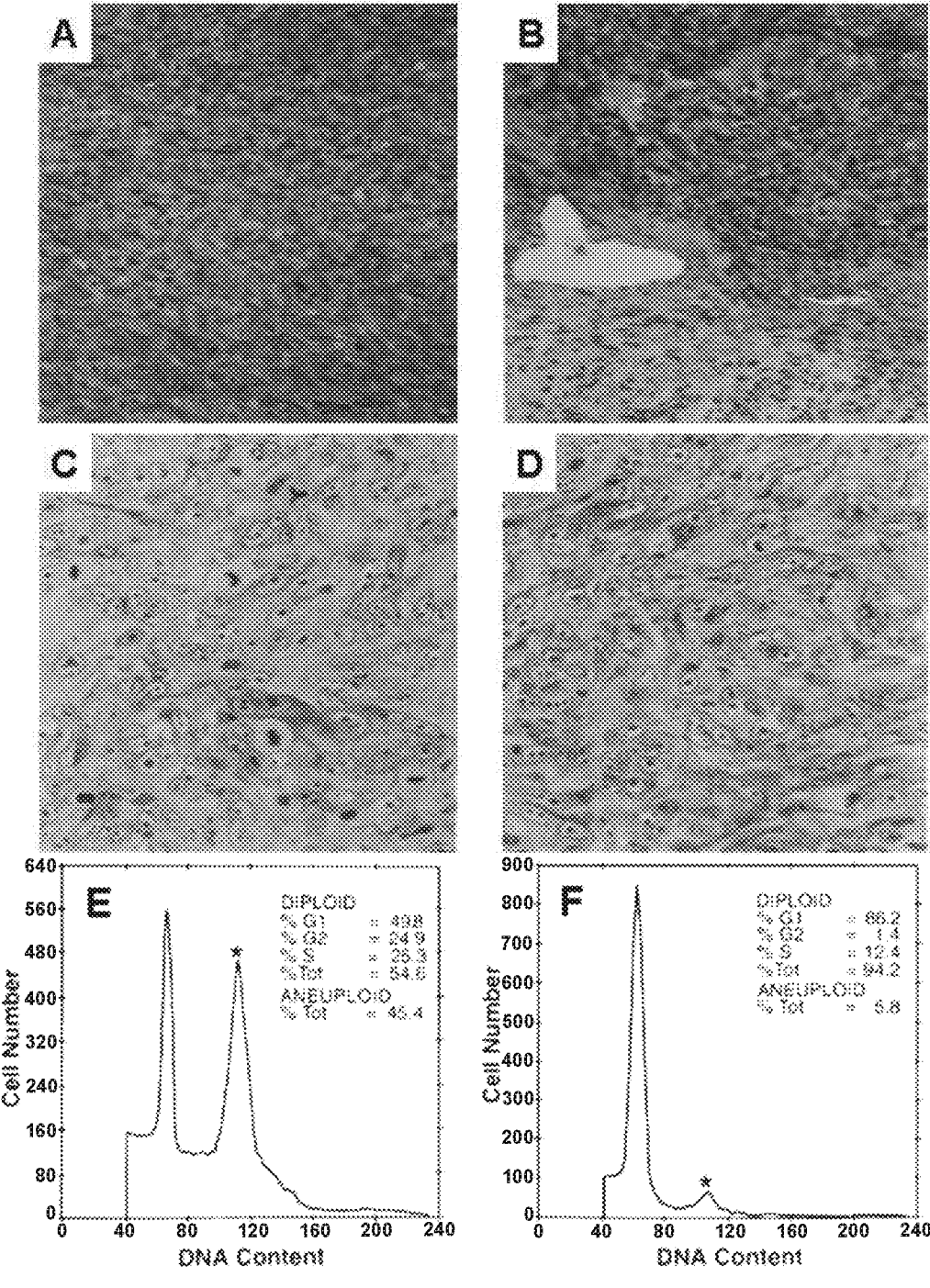
FIG. 6 represents stained images and fluorescence-activated cell sorting (FACS) analyses of MMNG/HOS tumor specimens. Trichrome (collagen)-stain of formalin-fixed MNNG/HOS tumor sections 2 days following a 10-day treatment with retroviral vectors bearing the control vector (panels A and C) or the as-cyclin G1 vector (panels B and D). Graphical representation of FACS analyses of PI-stained MNNG/HOS tumor cells that were control vector-treated (panel E) and as-cyclin Givector-treated (panel F) are shown.

Example 3—In Vivo Studies Using a Subcutaneous Human Osteosarcoma Model in Mice The in vivo therapeutic utility of the as-cyclin G1 vector was evaluated using human osteosarcoma tumors developed in nude mice. As shown in FIG. 5 panels A-C, daily injections of the as-cyclin G1 (G1aG1SvNa) vector significantly inhibited tumor growth over 10 days when compared to the control G1XSvNa vector (p<0.001; n=4 per group). Further, histological examination of the trichrome-stained stained tissue section of as-cyclin G1 (G1aG1SvNa) vector-treated tumors (FIG. 6 panels B and D) revealed increased stroma formation which accounted for a significant proportion of the residual tumors and a lower mean mitotic index (1.3±0.3%) than the control vector-treated tumors (FIG. 6 panels A and C). In contrast, the control vector-treated tumors showed minimal stroma formation with highly proliferative tumor cells with mean mitotic index of 3.5±1.0% (n=4000 cells counted in each group; p<0.001). In situ FACS analysis of cells obtained from as-cyclin G1 vector-treated tumors (FIG. 6 panel F) revealed a dramatic reduction in the number of cells exhibiting aneuploidy (2%) compared to 45% in control vector-treated tumors (FIG. 6 panel E), and an accumulation of diploid cells stationed in the G1 phase of the cell cycle, along with a corresponding reduction of the number of tumors in S, G2/M phases (FIG. 6 panel F) compared to the control (G1XSvNa) vector-treated tumors (FIG. 6 panel E), suggesting that the mechanism of cytostasis in the transduced cells accompanies a G1 phase cell cycle block.

Figure 7:
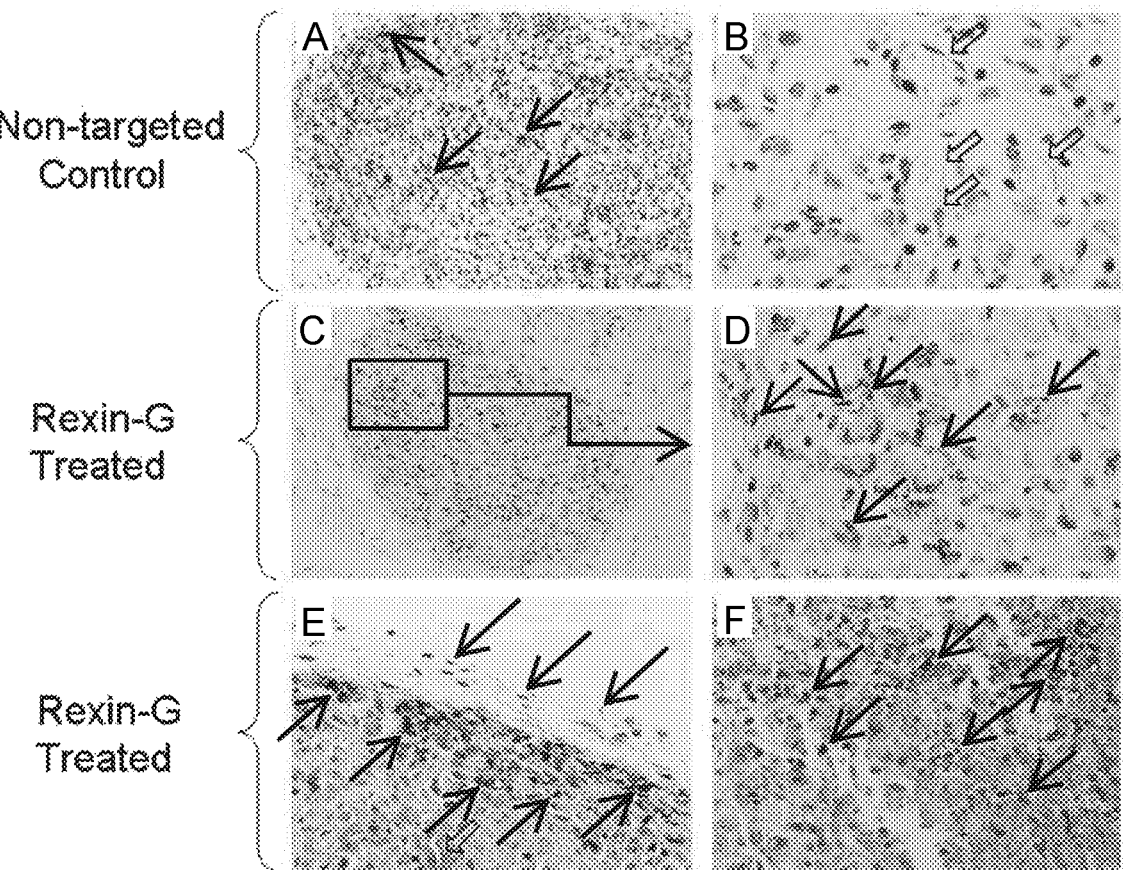
FIG. 7 shows microscopy images depicting apoptosis in tumor nodules treated with DeltaRex-G vector. Original magnification: panels A and C are ×40; panels B, D, E, and F are ×200.

Example 4—Effect of DeltaRex-G In Vivo Using a Subcutaneous Human Xenograft Model of Pancreas Cancer in Mice Apoptosis is a known consequence of cyclin G1 blockade in both neoplastic cells and hyperplastic vascular cells. Immunohistochemical staining of the tumors treated with the DeltaRex-G vector revealed a markedly increased incidence of TdT-mediated dUTP nick end labeling (TUNEL)-positive cells (FIG. 7), ranging from 5-36%, when compared with those of control-vector-treated mice. Tumor nodule from a control vector-treated animal (FIG. 7 panel A) revealed a low incidence of TUNEL-positive apoptotic cells (arrows) while a higher magnification of the same area (as shown in FIG. 7 panel B) showed areas of active angiogenesis devoid of TUNEL-positive cells (open arrows). Apoptosis was not detected in angiogenic vessels of control vector-treated mice. On the contrary, a tumor nodule from DeltaRex-G vector-treated mouse (FIG. 7 panel C) revealed an increased incidence of apoptosis as determined by the large number of TUNEL-positive cells. A higher magnification of the boxed area in FIG. 7 panel C revealed an abundance of TUNEL-positive endothelial cells (arrows) as shown in FIG. 7 panel D. Extensive apoptosis of tumor endothelial cells (36±5%) in areas of angiogenesis as well as in the stromal compartment was observed in the DeltaRex-G-treated animals (FIG. 7 panel E). A tumor nodule treated with numerous TUNEL-positive tumor cells (arrows) following DeltaRex-G vector treatment is shown in FIG. 7 panel F.

Example 5—Efficacy Studies Targeting Human Subcutaneous Xenograft Models of Pancreatic Cancer in Mice The efficacy of peripheral vein injection of a pathotropically-targeted vector (DeltaRex-G) versus a non-targeted retroviral vector (CAE-dnG1) bearing a cytocidal dominant-negative cyclin G1 construct, a control vector bearing a nuclear-targeted 11-galactosidase gene (designated Mx-nBg) or a PBS placebo was evaluated using an established human cancer xenografts model in nude mice. About $1 \times 10^7$ to $9 \times 10^7$ human MiaPaca2 pancreatic cancer cells (prototype for metastatic gastrointestinal cancer) were implanted subcutaneously into the flank of nude mice. Six days later, when measurable tumors had been established in the flanks of mice, 200 µL of the respective vector was infused directly into the tail vein daily for one or two 10-day treatment cycles. The size of the tumor was measured every 2-4 days with a Vernier caliper and the volume was calculated using the formula for the volume of ellipsoid objects: Tumor Volume $(mm^3) = 4/3 \pi r_1 r_2 r_3$. The animals were sacrificed using $CO_2$ inhalation and cervical dislocation, following which the tumor nodules were excised in toto and sectioned into two halves—one half quick-frozen in OCT blocks in liquid $N_2$ and the other half fixed in 10% formaldehyde prior to embedding and histological analysis.

Example 6—Evaluation of Gene Transfer Efficiency In Vivo

Transduction efficiency was determined by immunohistochemical staining of the tumor nodules, using a mouse monoclonal antibody directed against the ß-galactosidase antigen (GAL-40, Sigma, St. Louis Mo., USA) followed by analysis using an Optimas imaging system (Optimas Corporation, Bothell, Washington, USA). Transduction efficiency (expressed as %) was determined by counting the number of ß-galactosidase positive cells in three high power fields per tumor nodule, divided by the total number of cells×100. Table 1 shows the level of transduction of cells throughout the tumor nodules in Mx-nBg vector-treated animals.

TABLE 1

Transduction of cells within tumor nodules
in Mx-nBg vector-treated animal

| Animal No. | Total Number of Cells Counted | Number of Transduced Tumor Cells | Transduction Efficiency (%) |
|---|---|---|---|
| 1 | 2901 | 993 | 34.4 |
| 2 | 3002 | 1129 | 37.6 |
| 3 | 2359 | 811 | 34.3 |
| 4 | 3230 | 1175 | 36.3 |
| Mean ± S.D. | 2873 ± 319 | 1027 ± 142 | 35.7 ± 1.4 |

Cumulative vector dose: $6.9 \times 10^7$ cfu/25 g mouse.

12

Since only 25-45% of cancer cells are in S or M phase at a given time, the level of transduction reflects a potentially limiting but at the same time a built-in safety feature of retroviral vectors, i.e., the ability to transduce only actively dividing cells. Under light microscopy, both tumor and angiogenic endothelial cells were noted to be transduced by the Mx-nBg vector, indicating that a non-classical bystander effect could be induced by delivering a cytocidal gene into proliferative endothelial cells within the tumor nodule and thus depleting the tumor of its blood supply. Therefore, 100% transduction of tumor cells by a cytocidal vector is not considered to be necessary to achieve the desired control of tumor growth.

Example 7—Short-Term Efficacy Study Using DeltaRex-G

In a short-term efficacy study, IV infusions of either the Mx-nBg control vector, the non-targeted CAE-dnG1 vector, the DeltaRex-G cytocidal vector, or a placebo commenced six days after implantation of $1 \times 10^7$ human MiaPaca2 pancreatic cancer cells, and were continued daily for a total of 10 vector infusions. As shown in Table 2, progressive growth in tumor size was observed in mice treated with the Mx-nBg vector, the non-targeted CAE-dnG1 vector and placebo PBS, while significant tumor regression was observed in animals that were treated with the DeltaRex-G vector.

TABLE 2

Tumor growth characteristics

| Vector Name (No. of Animals) | Average Rate of Tumor Growth per Day (95% Confidence Interval) | p Value DeltaRex-G vs Control |
|---|---|---|
| DeltaRex-G (10) | −6.1% (−9.5%, −2.5%) | |
| Mx-nBg (4) | 6.3% (−0.3%, 13.4%) | 0.004 |
| CAE-dnG1 (4) | 4.1% (−3.3%, 12.1%) | 0.014 |
| PBS Placebo (3) | 12.0% (2.8%, 21.9%) | 0.001 |

Cumulative vector dose: $5.6 \times 10^7$ cfu/25 g mouse.
PBS vs. Mx-nBg: p = 0.37;
PBS vs. CAE-dnG1: p = 0.10

Example 8—Long-Term Efficacy Study Using DeltaRex-G

Figure 8:
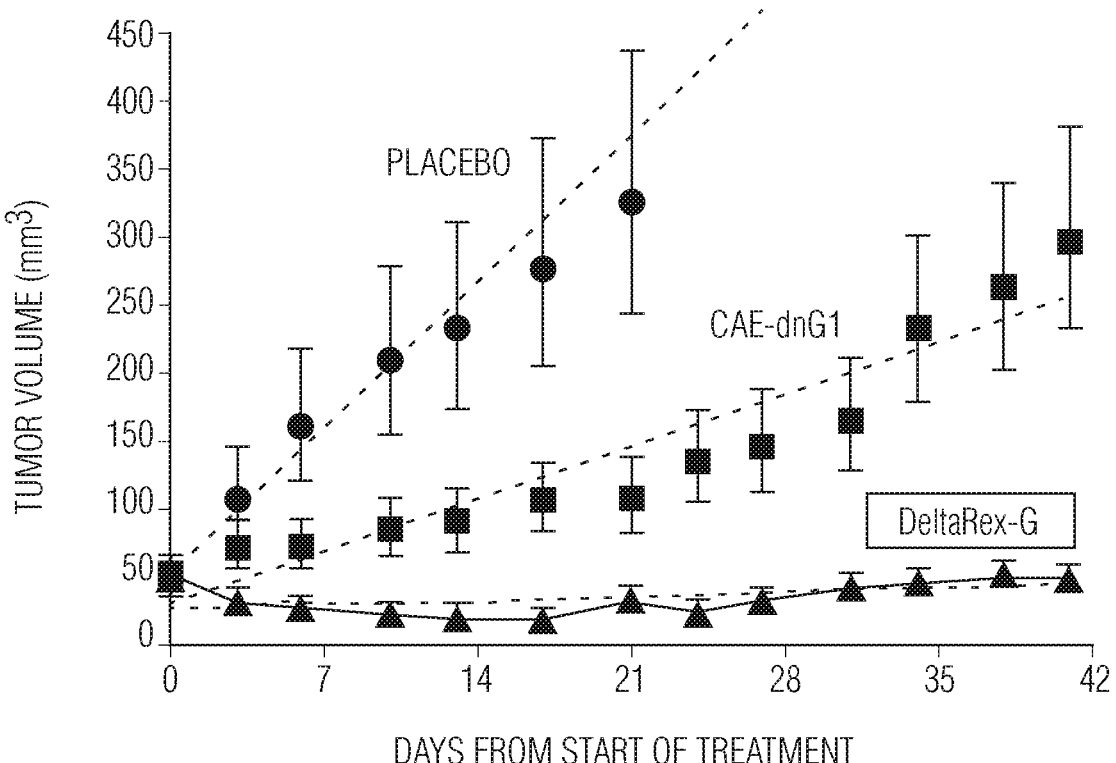
FIG. 8 is a graphical representation of tumor volume over days from start of treatment in human MiaPaca2 xenograft model of pancreas cancer in nude mice. Treatment groups shown are: PBS control ("Placebo"); CAE-dnG1 control vector bearing a non-targeted dominant negative anti-cyclin G1 construct; DeltaRex-G targeted vector bearing a dominant negative anti-cyclin G1 construct.

An additional 10-day treatment cycle with the DeltaRex-G vector (cumulative vector dose: $1.6 \times 10^8$ cfu/mouse), a similar dose of a non-targeted CAE-dnG1 vector, or an equal volume of PBS placebo, was given after an intervening rest period, which confirmed that the observed therapeutic efficacy was entirely dependent upon the pathotropic matrix-targeting motif incorporated by genetic engineering into the primary structure of the amphotropic MLV envelope protein. During the first treatment cycle, a rapid increase in tumor size was noted in the placebo-treated mice, while no significant inhibition of tumor growth was observed in the non-targeted CAE-dnG1 vector-treated animals when compared to the PBS control (Table 2). In contrast, rapid tumor regression was noted as early as the $4^{th}$ treatment day with the DeltaRex-G vector. During the first treatment cycle, the rate of tumor growth was significantly inhibited in the DeltaRex-G vector-treated mice compared to the non-targeted CAE-dnG1 vector-treated-mice, the control targeted Mx-nBg vector-treated, and the PBS-treated mice (Table 2). During and after the second treatment cycle as shown in FIG. 8, the tumor growth rate in DeltaRex-G vector-treated mice remained consistently slower than that of the non-targeted CAE-dnG1 vector-treated animals throughout the 7-week follow-up period.

Example 9—Efficacy Studies in Mouse Model of Liver Metastasis

In this study, the anti-tumor effects of serial portal vein infusions of pathotropic matrix-targeted vectors bearing a cytocidal dominant negative cyclin G1 (dnG1) construct were assessed in a pancreatic cancer model of liver metastasis. Two pathotropic retroviral vectors were used (DeltaRex-G [formerly Mx-dnG1], and MxV-dnG1). In vivo efficacy studies were conducted in compliance with a protocol approved by the University of Southern California Institution Animal Care and Use Committee. To evaluate the efficiency of targeted gene delivery based on the anti-tumor effects and DeltaRex-G or MxV-dnG1 vector treatment in vivo, a model of liver metastasis simulating the route of dissemination of human pancreatic cancer was established in nude mice. Briefly, $7\times10^5$ tumor cells were infused slowly into the portal vein via an indwelling catheter, which was kept in place for 14 days. Four treatment groups were compared: DeltaRex-G, also known as Bv1/dnG1 or Mx-dnG1 (cumulative vector dose: $5.4\times10^6$ cfu); MxV-dnG1, also known as Hs2A/SVG/dnG1 (cumulative vector dose: $1.7\times10^9$ cfu); a control vector bearing a ß-galactosidase (nBg) gene (cumulative dose: $1.5\times10^9$ cfu); and PBS control. The resulting Kaplan-Meier curves indicate that prolonged survival is dependent on the targeting envelope as well as the therapeutic payload.

For histological and morphometric analysis, the liver lobes were excised, fixed in 10% formalin, labeled A for the right and caudate lobes, B for the left lobe and C for the median lobe, processed separately and embedded in paraffin blocks. The anti-tumor efficacy of DeltaRex-G, MxV-dnG1 or control vector treatment was assessed as follows: H & E stained tissue sections were examined by light microscopy, and the surface areas of representative liver sections and tumor foci from lobes A, B and C were measured by morphometric analysis using an Optimas image analysis system.

For statistical analysis, the response variables, total surface area (S.A.) of liver, total S.A. of tumor, S.A. tumor to S.A. liver ratio, and mean S.A. tumor foci, were log transformed prior to formal analysis. A repeated measures analysis with lobe as the repeated measures factor was used to determine whether or not the treatment had an effect on each of the response variables. Pair-wise comparisons were also performed for the outcome variables with overall F-test p-values<0.05 between groups.

Figure 9:
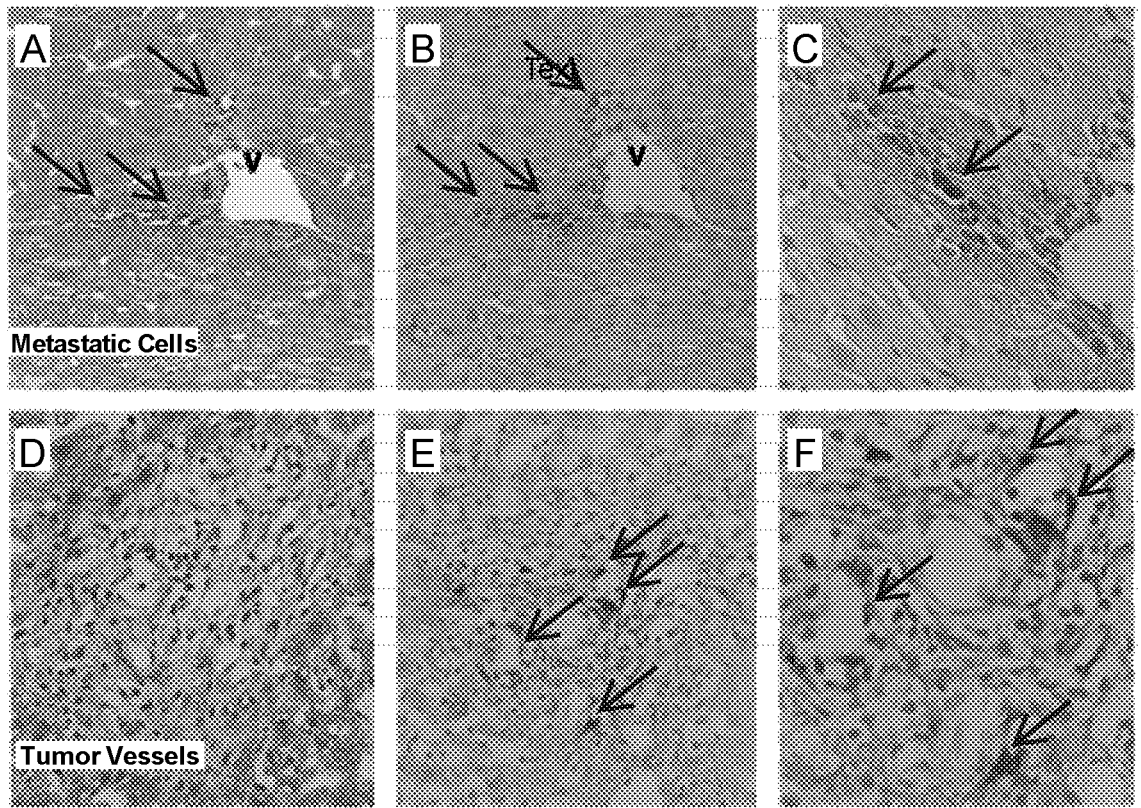
FIG. 9 shows photomicrographs depicting Transgene expression in tumor cells and tumor endothelial cells in vivo in a human xenograft model of pancreas cancer metastatic to liver in nude mice. Panel A depicts H&E stain of tumor cells invading the liver shown at 20× magnification; panel B depicts nuclear b galactosidase transgene (blue-staining) expression in tumor cells indicating successful gene transfer shown at 20× magnification; panel C depicts panel B at 200×; panel D shows an H&E stain of tumor endothelial cells at 20×; panel E depicts nuclear b galactosidase transgene (blue-staining) expression in tumor endothelial cells indicating successful gene transfer shown at 20× magnification; and panel F shows panel E at 200× magnification.

Morphometric analysis of tumor foci showed that that portal vein infusions (via indwelling catheter) of pathology-targeted dnG1 vectors induced significant reductions in the sizes of tumor foci when compared to the PBS- and control vector-treated animals based on all response variables (p<0.0002). In pairwise comparisons for the three outcome variables, a dose-dependent tumor response to dnG1 vector treatment was apparent. FIG. 9 shows the performance of the matrix-targeted vector bearing a β-galactosidase marker gene (Mx-nBg; blue staining material), demonstrating (i) the precision pathotropic targeting of pancreatic cancer cells at the earliest stages of liver metastasis (FIG. 9 panels A, B, and C) and (ii) the proliferative endothelial cells of the tumor-associated vasculature (FIG. 9 panels D, E, F), while sparing normal differentiated cells of the liver parenchyma.

Figure 10:
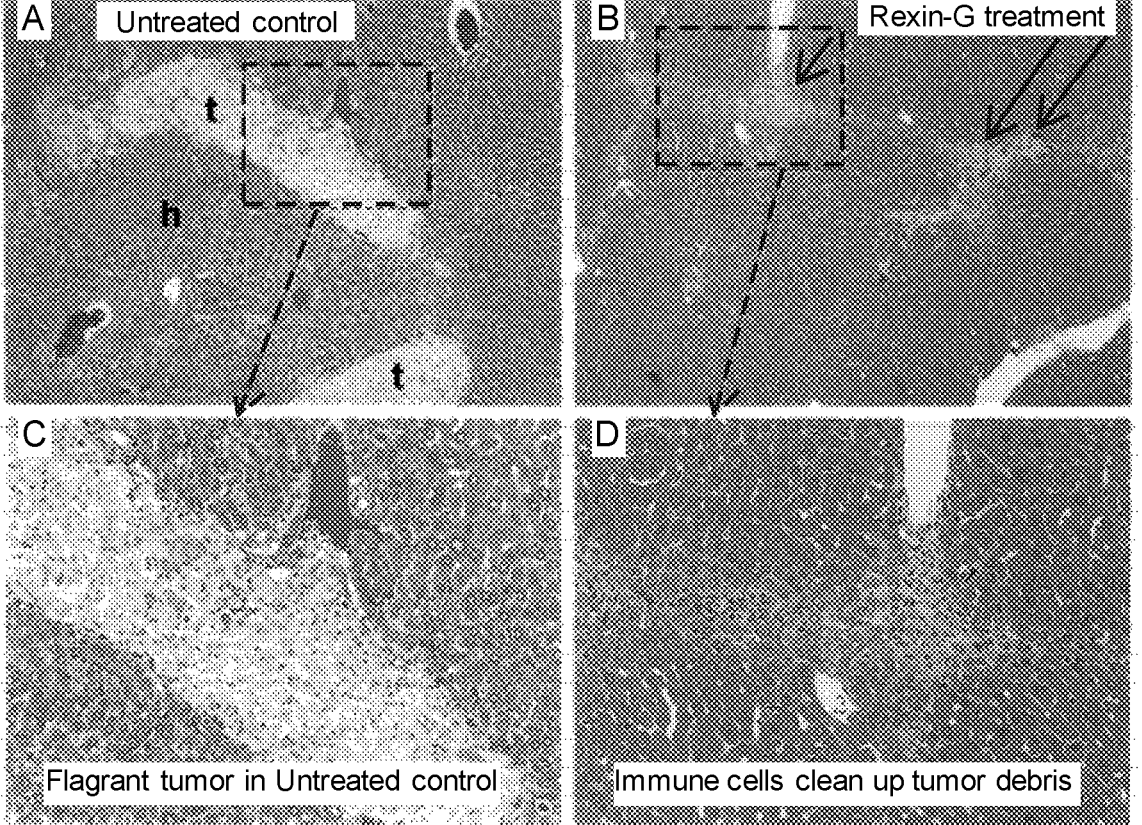
FIG. 10 shows microscopy images of specimens from untreated control (panels A and C) and DeltaRex-G (formerly Rexin-G)-treated animals (panels B and D). Panels C and D are magnified images of panels A and B respectively.

Dose-dependent efficacy of tumor-targeted vector was also indicated. Morphometric analysis of tumor foci confirmed that the targeting strategy for therapeutic gene delivery was effective in that portal vein infusions (via indwelling catheter) of high dose DeltaRex-G induced dramatic reductions in the sizes of tumor foci when compared with the PBS and control vector-treated animals based on all response variables (p<0.0002). In pairwise comparisons for the three outcome variables, a dose-dependent tumor response to DeltaRex-G was apparent (mean tumor SA low dose group=0.012, n=12; high dose group=0.006, n=12). FIG. 10 shows the performance of the DeltaRex-G vector bearing a dominant negative cyclin G1 construct. Whereas control animals (FIG. 10 panels A and C) exhibited an abundance of flagrant tumors, animals treated with repeated infusions of DeltaRex-G (FIG. 10 panels B and D) exhibited a dose-dependent reduction of tumor burden which approached that of complete tumor eradication. Importantly, the resident immune cells (Kupffer cells) are seen to be engorged with haemosiderin, exemplifying their role in 'cleaning up' the tumor debris.

Figure 11A:
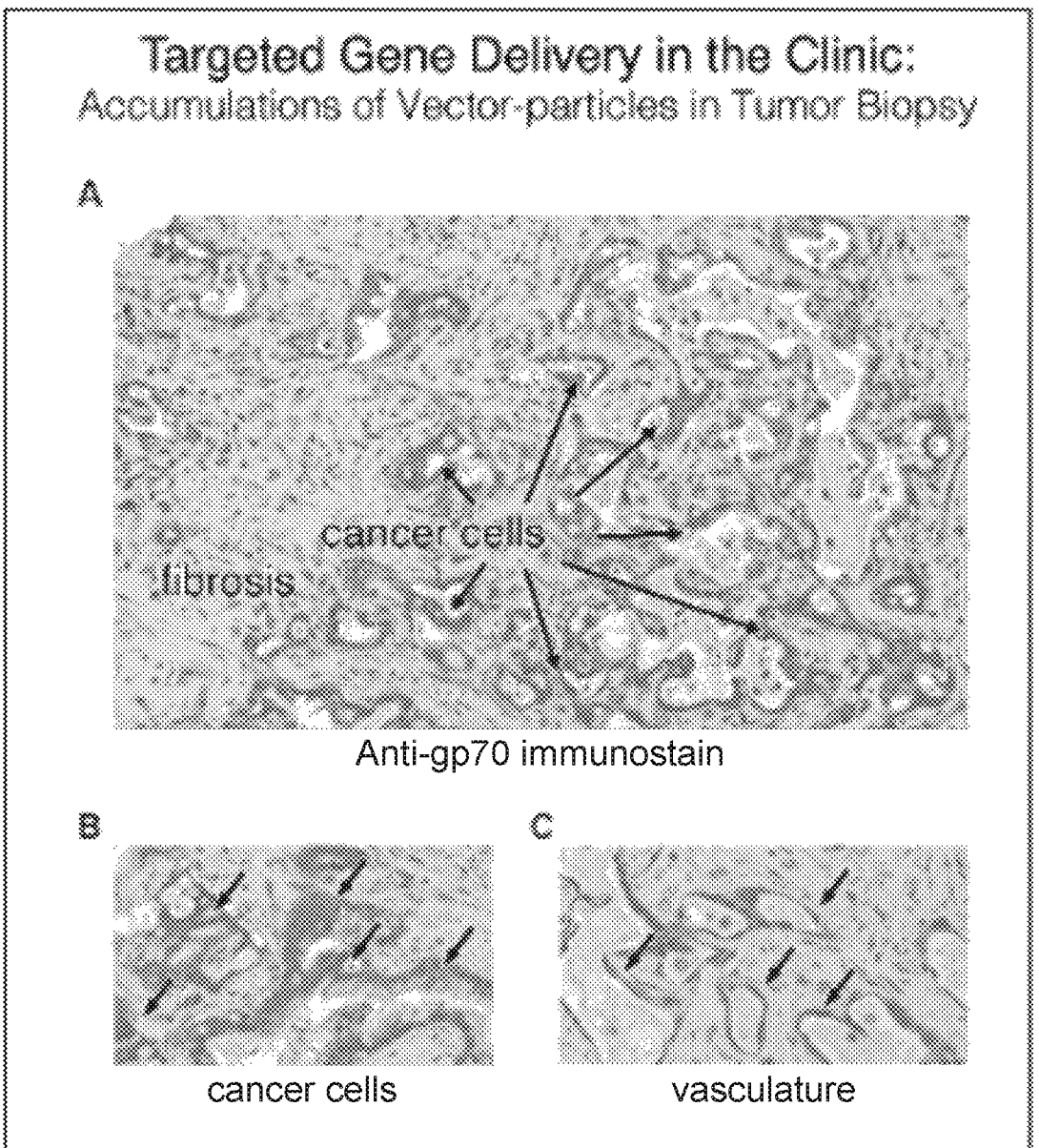
FIG. 11A shows images of immunohistochemical (IHC) analyses of a DeltaRex-G treated metastatic liver nodule. Panel A shows images IHC staining for the retrovector gp70+ env protein (brown stain). Higher magnification images of IHC staining for retrovector gp70+ env protein in human cancer cells (panel B, arrows) and tumor vasculature (panel C, arrows) are shown.
Figure 11B:
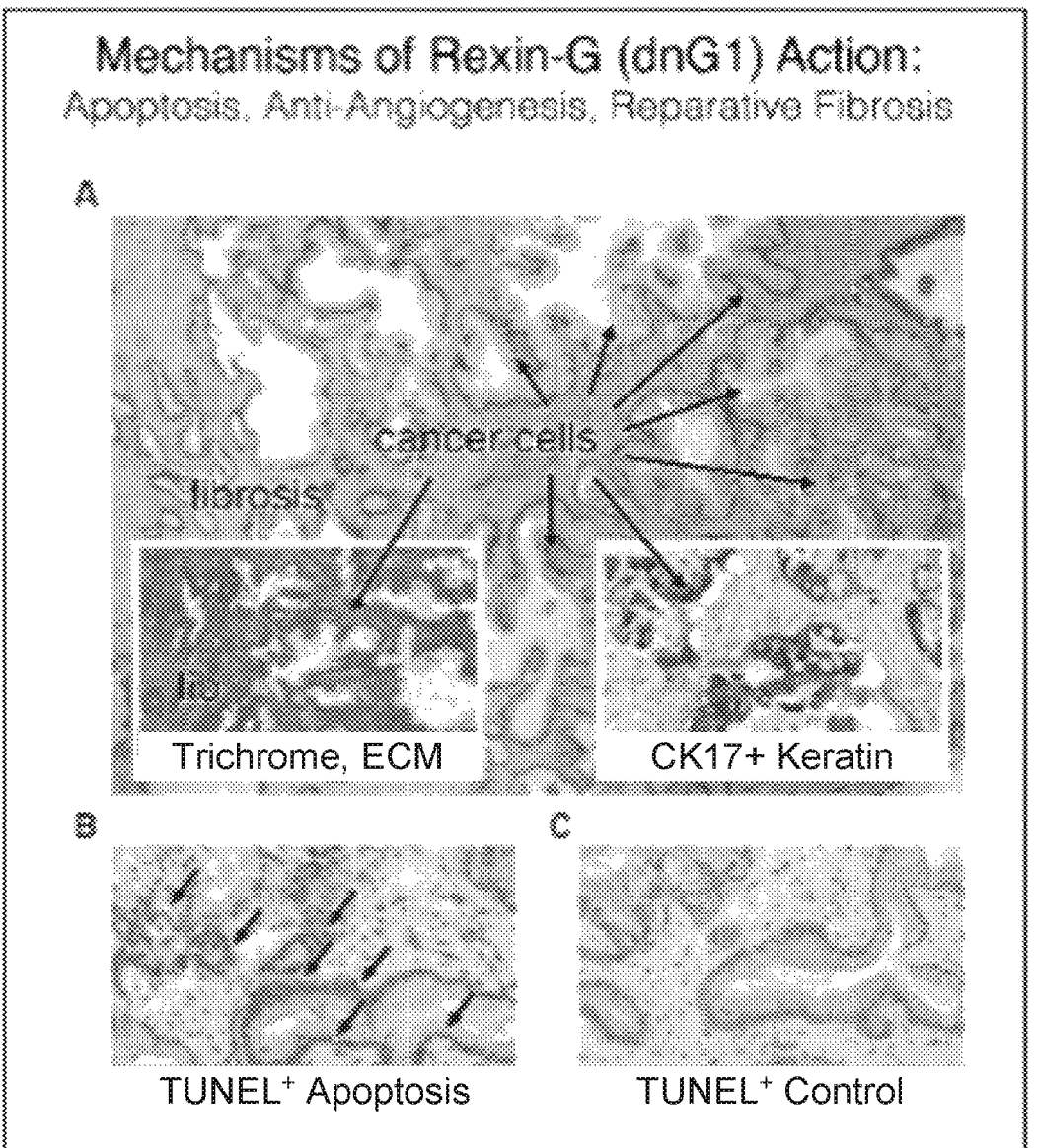
FIG. 11B shows images of IHC analyses of a DeltaRex-G treated metastatic liver nodule. Panel A shows an image of H&E stained specimen. Reactive fibrosis is seen with trichrome stain (panel A, inset on left, blue), and residual CK17+ cancer cells (panel A inset on right). Panel B depicts an image of TUNEL$^+$ apoptotic cancer cells (arrows) in residual tumor. Panel C depicts an image of an immunohistochemical control.

Example 10—Testing Tumor-Targeted Gene Delivery and Cytocidal Bioactivity in Human Pancreatic Cancer In a Phase 1/2 study of DeltaRex-G for gemcitabine-resistant pancreatic cancer, a patient was given 4 treatment cycles, each cycle consisting of i.v. infusions of DeltaRex-G three times a week. Once metastatic spread was demonstrably contained, and only a solitary liver lesion remained active via PET/CT scan, surgical excision of residual tumor was performed. Immunohistochemical analysis shows penetration/accumulation of immunoreactive vector particles (gp70 env) within tumor cells and tumor vasculature (FIG. 11A). Furthermore, a significant amount of apoptosis (~50%) of tumor cells/vasculature was observed within the TME as a direct result of DeltaRex-G cytocidal bioactivity (FIG. 11B).

Figure 12:
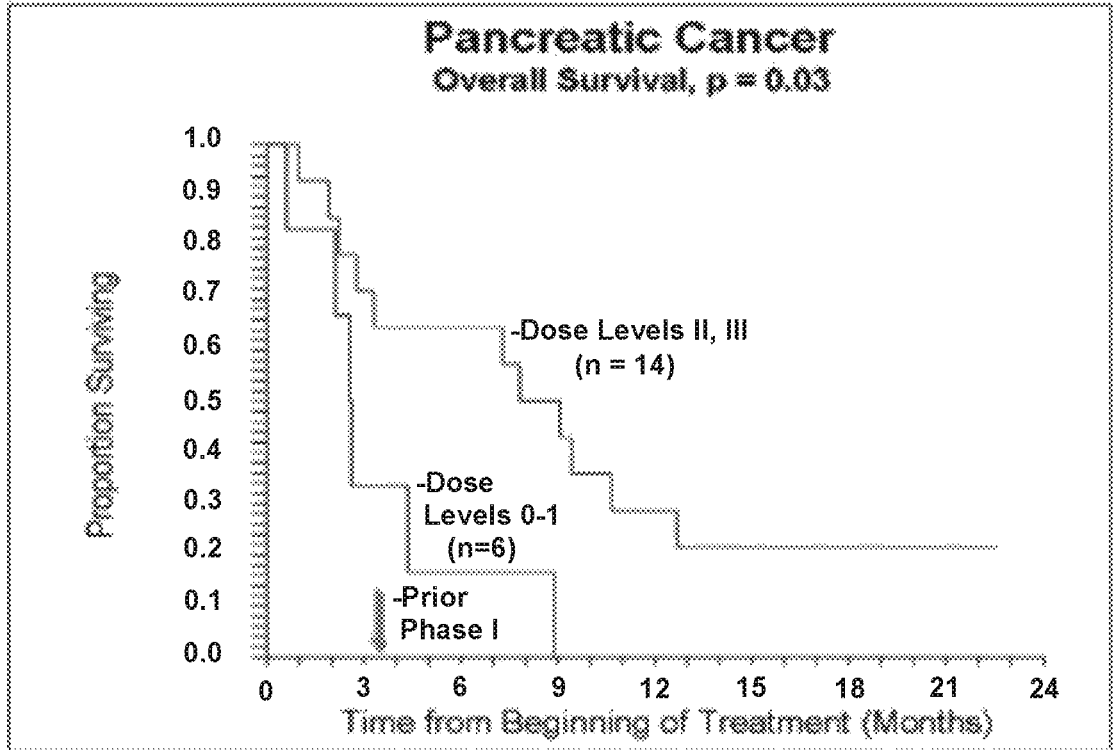
FIG. 12 is a graphical representation of a Kaplan Meier analysis of overall survival in patients treated with escalating doses of DeltaRex-G.

Example 11—Testing Dose/Response Relationship Between DeltaRex-G and Patient Survival In a Phase 1/2 study using DeltaRex-G in patients with metastatic, chemotherapy-resistant pancreatic cancer, a dose-response relationship was observed between overall survival and DeltaRex-G dose. While the requisite low-dose levels employed in a prior Phase 1 safety study failed to improve the dismal survival statistics for pancreas cancer, these progressive FDA-approved dose-escalations served to improve the median OS to 9.3 months with a one-year overall survival rate of 29% (FIG. 12). FIG. 12 shows the proportion surviving (Y axis) plotted over time from start of treatment (X axis). Further quantitative analysis indicated that a Calculus of Parity, (or functional equivalence), which attempts to match a given tumor burden with a (calculated) cumulative dose of DeltaRex-G, may be a useful predictor of long term outcome.

Figure 13:
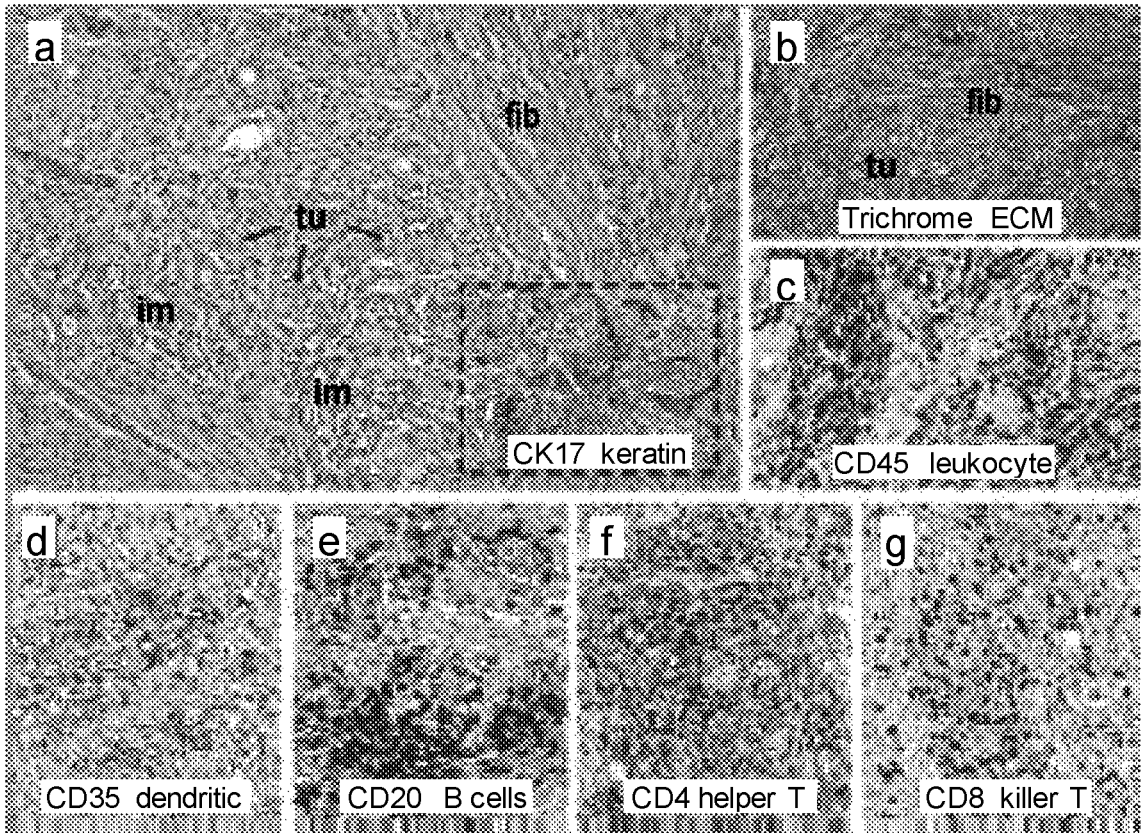
FIG. 13 represents immunohistochemical images of a residual tumor. Panel a shows hematoxylin and eosin stain of tumor nodule with CK17+ cancer cells (boxed), tumor cells (tu), fibrosis (fib), and immune cells (im). Panel b is an image of a residual tumor with a trichrome stain for new collagen (blue staining material), extracellular matrix (ECM). Images representing cells expressing the CD45+ leukocyte common antigen (panel c), CD35+ dendritic cells (panel d), CD20+ B cells (panel e), CD4+ helper T cells (panel f), CD8+ killer T cells (panel g) are shown (reddish brown staining material in panels c-g).

Example 12—Immune Cell Trafficking and Activity in Residual Tumors of DeltaRex-G Treated Patients A cancer patient in a Phase 1/2 study underwent resection of a residual tumor nodule after three treatment cycles of DeltaRex-G. Immuno-cytochemical phenotyping of the tumor-infiltrating lymphocytes showed CD35+ dendritic cells, CD20+ B cells, CD4+ helper T cells, and CD8+ killer T cells in the TME (FIG. 13). The preponderance of tumor-infiltrating lymphocytes in the TME supports the potential for utilizing DeltaRex-G in combination with immune-modulatory agents.

DeltaRex-G can be given safely in the clinical setting of activated T cells evoked by combinatorial therapy using DeltaRex-G and Reximmune-C, XC targeted retrovector encoding a cytokine (GM-CSF) gene. In a Phase 1/2 study, 16 patients with chemo-resistant Stage 4 cancer, and 2 chemo-naïve patients received DeltaRex-G, $2\times10^{11}$ cfu, on Days 1, 3, and 5, plus Reximmune-C, 0.5 or $1.0\times10^{10}$ cfu on Day 3 (Dose I, II, III respectively), and valacyclovir at 2-3 gms/day p.o. on Days 6-19, comprising one cycle. No systemic toxicity was noted in this setting of activated immune system.

Figure 14:
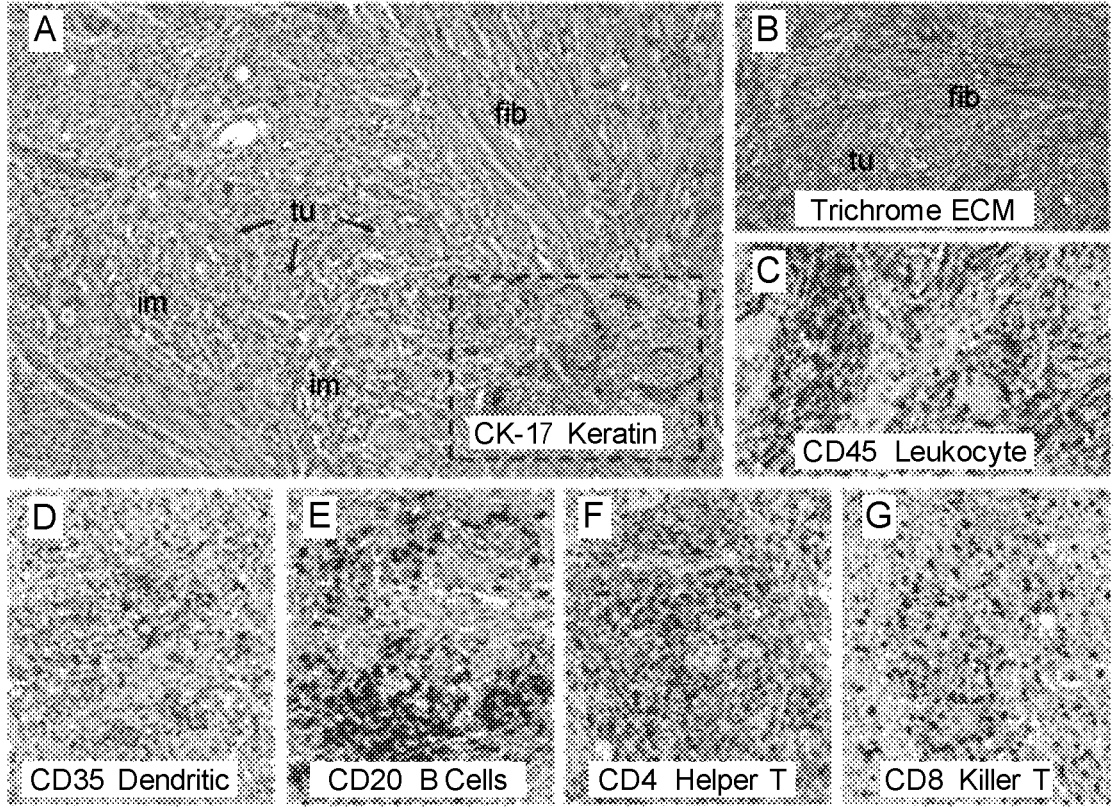
FIG. 14 represent images of hematoxylin and eosin (H&E) stained specimen (panel A), CEA+ tumor cells (panel B), immunoreactive GM-CSF transgene (reddish-brown staining material) in a necrotic tumor (panel C), MPO staining granulocytes (panel D), CD4+ (panel E), CD8+ (panel F) and CD20+ (panel G) tumor infiltrating lymphocytes (TILs).
Figure 15:
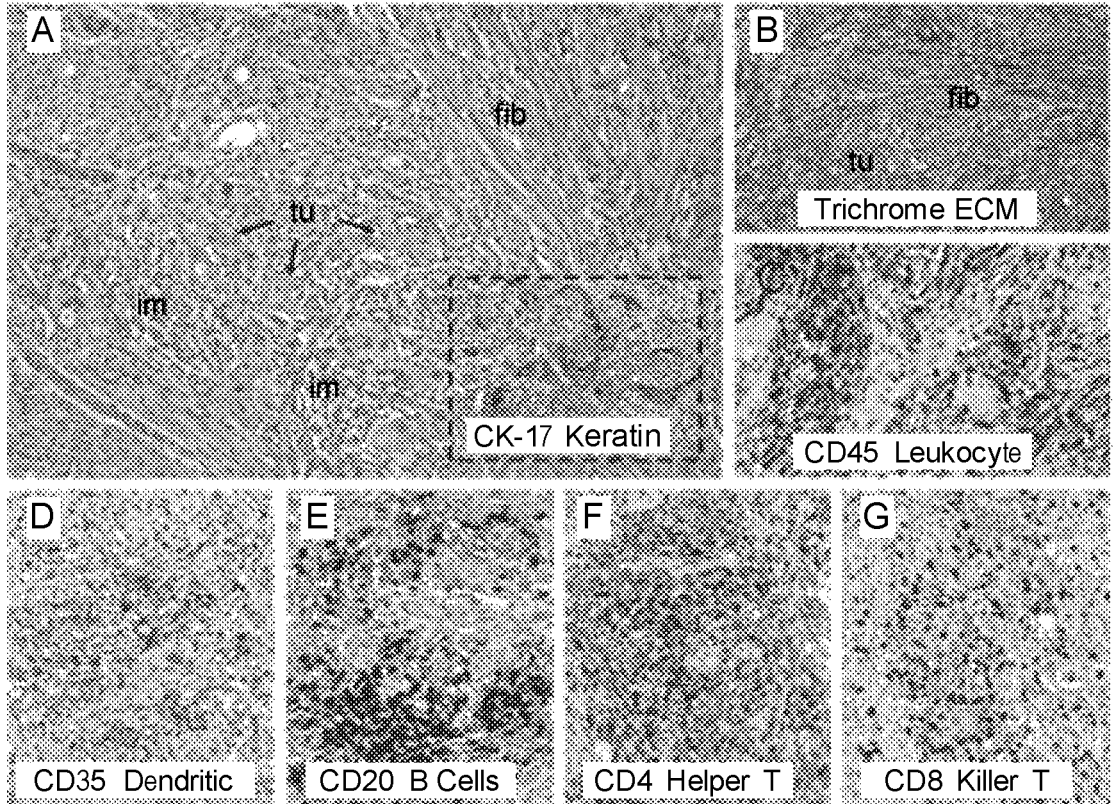
FIG. 15 depicts immunohistochemical images of a tumor. Tumor nodule with a H&E stain (panel A), cytokeratin-17 immunostain (panel A inset), trichome stain for collagenous material (panel B), leukocyte common antigen (panel C), CD35+ for dendritic cells (panel D), CD20+ for B cells (panel E), CD4+ for helper T cells (panel F), and CD8+ for killer T cells (panel G) are shown. ECM, extracellular matrix; fib, fibrosis; im, immune cells; tu, tumor.

Residual tumor was resected two days after infusion of DeltaRex-G and Reximmune C targeted retrovector bearing a cytokine gene (GM-CSF) from a Stage-4 colon cancer patient. Tumor infiltrating lymphocytes (TILs) and cytokine transgene expression in the TME are shown (FIG. 14 and FIG. 15). Areas of tumor necrosis with TILs, CEA+ tumor cells, immunoreactive GM-CSF transgene in a necrotic tumor, MPO staining granulocytes, CD4+, CD8+ and CD20+ TILs, suggesting recruitment of patient's tumor infiltrating lymphocytes into the residual tumor was observed.

Figure 16:
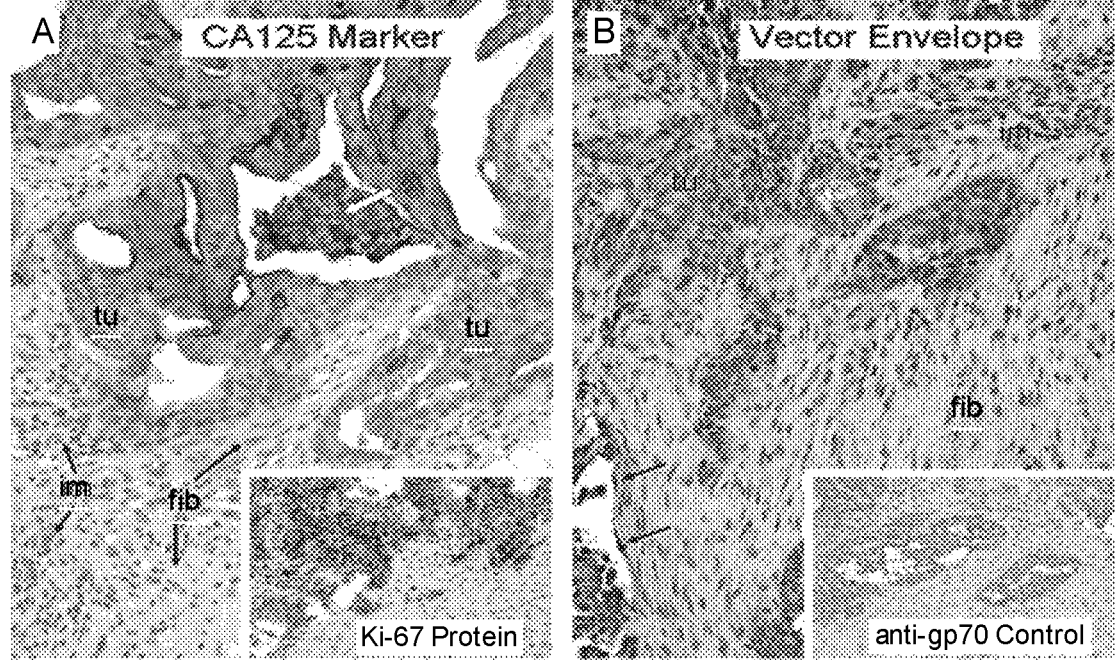
FIG. 16 represent microscopy images of post-DeltaRex-G treatment pelvic tumor specimens stained for CA125 (panel A), Ki-67 protein (panel A inset), DeltaRex-G nanoparticle vector envelope (brown staining material) (panel B), and anti-gp70 control (panel B inset) are shown. Localization of DeltaRex-G Nanoparticles in Residual Tumor of a Patient with Metastatic Ovarian Cancer. The residual pelvic tumor was resected two hours after intravenous infusion of DeltaRex-G. (A) Residual tumor (tu) marked by CA-125 surrounded by tumor infiltrating lymphocytes (im) and fibrosis (fib); (B) Immunoreactive DeltaRex-G nanoparticles in tumor nests and tumor vasculature (brown staining material).

Intravenous DeltaRex-G has minimal systemic toxicity due to its targeting properties that limits the biodistribution of DeltaRex-G only to areas of injury where exposed collagenous (XC) proteins are abnormally found. A residual pelvic tumor from a patient with metastatic ovarian cancer was resected two hours after intravenous infusion with DeltaRex-G. FIG. 16 shows localization of DeltaRex-G nanoparticles in the residual tumor. Residual tumor (tu) marked by CA-125 surrounded by tumor infiltrating lymphocytes (im) and fibrosis (fib) is shown (FIG. 16 panel A) with immunoreactive DeltaRex-G nanoparticles in tumor nests and tumor vasculature (brown staining material; FIG. 16 panel B).

Figure 17A:
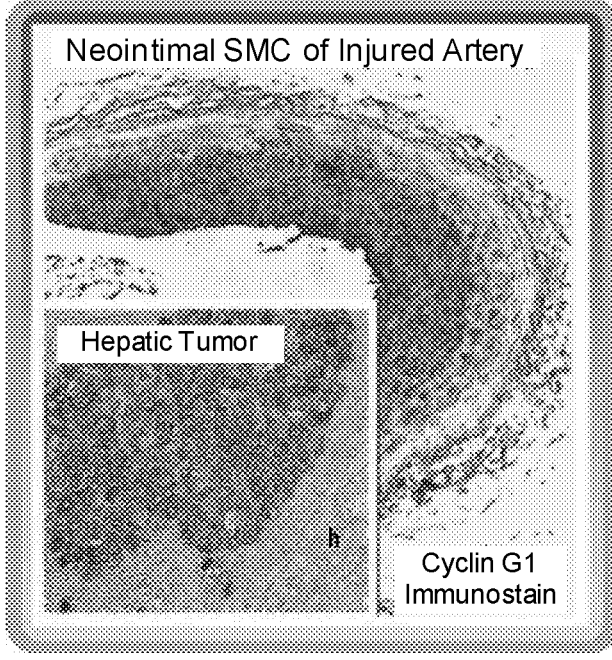
FIG. 17A represent images of neointimal smooth muscle cells of injured artery and hepatic tumor (inset) immunostained with cyclin G1.
Figure 17B:
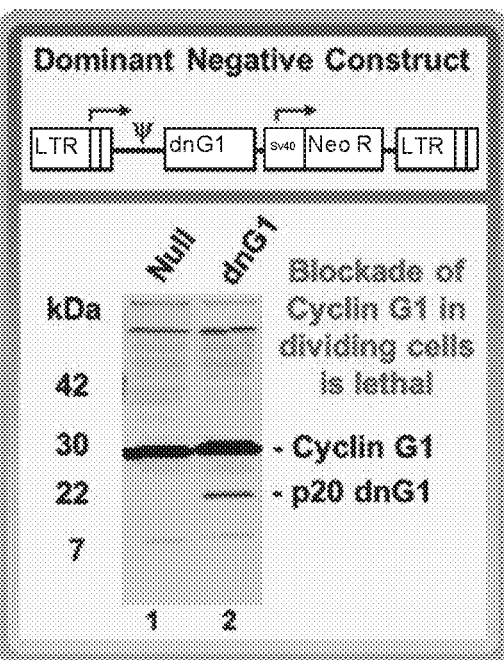
FIG. 17B shows an illustration of dominant negative construct (top panel) and a western blot image for cells transduced with DeltaRex-G or null (bottom panel).

Example 13—Testing the Targeting of DeltaRex-G in Balloon-Injury Rat Carotid Artery Model of Vascular Stenosis Injured arteries from a rat carotid injury model of vascular stenosis were immunostained with cyclin G1. Intense immunoreactive cyclin G1 expression in neointimal smooth muscle cells was as intense as immunoreactive cyclin G1 expression in a nude mouse model of liver metastasis (FIG. 17A inset). Furthermore, that A10 aortic smooth muscle cells can be transduced with DeltaRex-G was shown by the appearance of the dominant negative mutant cyclin G1 (p20 dnG1) protein 48 hours (Lane 2) (FIG. 17B).

Figure 18:
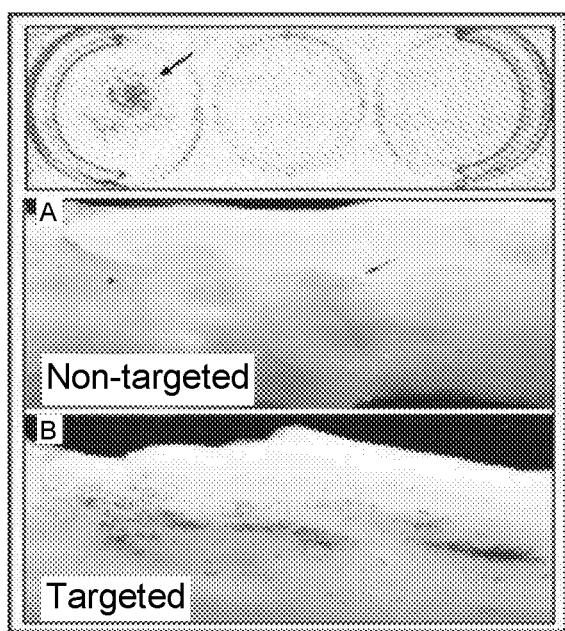
FIG. 18 shows an image of aortic smooth muscle cells overlaid on vector-treated collagen-coated wells (top panel), an image of an injured artery (middle panel), and an image of a balloon-injured rat artery following tail vein injections of a collagen-matrix targeted retrovector encoding a B galactosidase marker gene, Mx-nBg (blue-staining material; bottom panel).

The transduction of a targeted vector bearing nuclear B galactosidase gene construct, Mx-nBg, was tested on aortic smooth muscle cells. Effective transduction of A10 aortic smooth muscle cells overlaid on vector-treated collagen-coated wells was shown by the appearance of the nuclear B galactosidase transgene (blue-staining material) in collagen-plated well following transduction with Mx-nBg (FIG. 18 top panel; arrow), versus no transgene in wells transduced with a non-targeted or targeted null control vector. Further, when Mx-nBg was injected in the tail veins of a balloon injury rat carotid injury model of vascular stenosis, effective transduction of injured carotid artery was observed (blue-staining material, FIG. 18 bottom panel) while there were slight to no transduction with the non-targeted vector (FIG. 18 middle panel).

Figure 19:
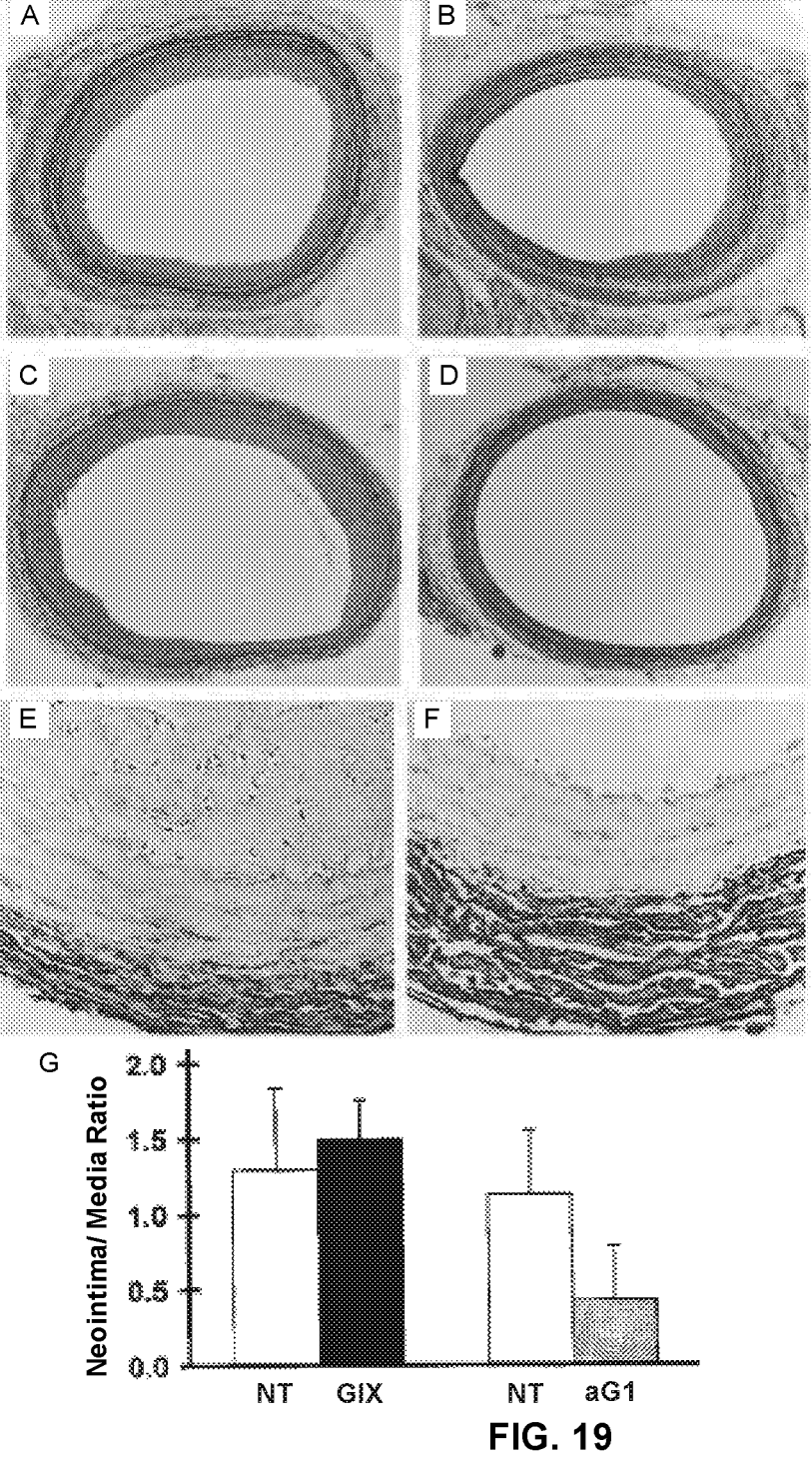
FIG. 19 show images of injured arteries (panels A-F) and a graph showing neointima/media ratio (panel G). Images of injured arteries from balloon-injury rat carotid artery model of vascular stenosis treated with control untreated (panel A), non-targeted (NT) (panels B, E, G), targeted null vectors GIX (panels C, F), and a targeted vector encoding an antisense cyclin G1 inhibitor, aG1 (panel D) are shown.

A balloon-injury rat carotid artery model of vascular stenosis was also treated with a targeted vector encoding an antisense cyclin G1 inhibitor, aG1. Abundant neointima was formed in control untreated (FIG. 19 panel A), non-targeted (NT) (FIG. 19 panels B, E, G) and targeted null vectors (GIX) (FIG. 19 panels C, F, G) while no neointima formation is seen in injured arteries treated with a targeted vector encoding an antisense cyclin G1 inhibitor, aG1 (FIG. 19 panel D).

Example 14—Testing DeltaRex-G on Laser-Treated Rabbit Corneas

The in vivo efficacy and safety of a retroviral vector bearing an antiproliferative dominant negative mutant cyclin G1 (dnG1) construct, when used for the prevention of corneal haze after phototherapeutic keratectomy (PTK), was studied. For in vivo efficacy studies, a 6-mm-diameter, 150-mm-deep transepithelial PTK, performed with a clinical 193-nm ArF excimer laser (VISX Star2, Santa Clara, CA) was performed on the left eyes of 20 adult New Zealand White rabbits. The surgically altered eyes were subsequently treated with eye drops containing: a retroviral vector bearing a dnG1 construct (dnG1; n=7), a control retroviral vector (null vector) bearing only the neomycin resistance, neor, gene (n=7), or a retroviral vector bearing an antisense cyclin G1 (aG1) construct (n=6). The time of closure of the corneal epithelial defect was monitored daily with fluorescein staining. Corneal haze was evaluated before surgery and at 2, 3, and 4 weeks after surgery, with a digital imaging system. Biodistribution studies for detection of potential vector dissemination to nontarget organs were conducted by PCR-based assay.

The re-epithelialization rate was similar among treatment groups, with complete closure of the corneal epithelial defect at 72 hours (P>0.05). Significant corneal haze developed in the null and aG1 vector-treated groups (P<0.05) at 3 to 4 weeks after PTK. In contrast, development of corneal haze was inhibited in the dnG1 vector-treated group when compared with the null vector-treated group (P<0.05). In parallel, a dramatic reduction to complete abrogation of abnormal extracellular matrix production was noted in the dnG1 vector-treated corneas when compared with the null and aG1 vector-treated groups. Biodistribution studies showed no evidence of vector dissemination in neighboring and distant organs. In conclusion, at therapeutic doses, eye drop application of the dnG1 retroviral vector is safe and effective in inhibiting development of corneal haze after PTK in rabbits.

Figures 20, 21:
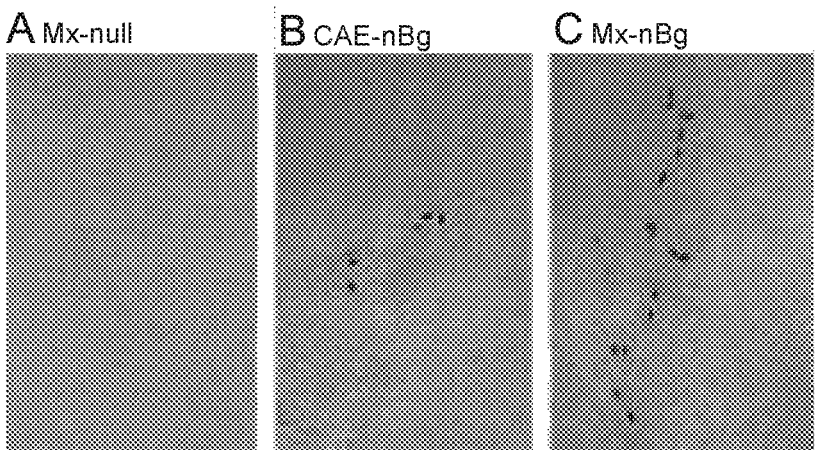
FIG. 20 show images of laser-injured corneas treated with eye drop applications of a null vector (panel A), a nontargeted (designated CAE-nBg) (panel B), or a collagentargeted (designated Mx-nBg) vector bearing a B-galactosidase gene (panel C).
FIG. 21 show images representing corneal transparency at preoperative status (top panels) and 4 weeks after phototherapeutic keratectomy (PTK) with retroviral vector instillation (lower panels). Corneal haze from DeltaRex-G (dnG1) (left panels), aG1 (middle panels), and null control (right panels) are shown.

A collagen-targeted vector was also tested for efficacy on injured corneas. Four rabbits underwent laser surgery and received eye drop applications of either a nontargeted (designated CAE-nBg) or a collagen-targeted (designated Mx-nBg) vector bearing a B-galactosidase gene. The cumulative vector dose for each rabbit in both groups was approximately $1\times10^7$ CFU administered over 2 days. Topographic examination of the laser-injured corneas showed an apparent increase in the number of transduced cells in corneas that were treated with the collagen-targeted vector (n=2) when compared with corneas that received the non-targeted vector (n=2), as evidenced by a fourfold increase in the number of B-galactosidase-expressing cells (FIG. 20, blue dots). There was no B-galactosidase-positive staining noted in the conjunctiva or in the corneal endothelium. These results indicate that improved retroviral gene delivery to laser-treated cor-
neas is dependent on the von Willebrand factor's targeting
motif displayed on the retroviral env protein.

Based on this finding as well as on previous reports,
DeltaRex-G, a collagen-targeted vector bearing a dnG1
construct was used for the in vivo efficacy studies. After
laser surgery, each rabbit received a topical cumulative
vector dose of $5\times10^7$ CFU as eye drops. On evaluation 2
weeks after laser treatment (12 days after vector applica-
tion), transient changes in corneal transparency were noted
in all three groups (FIG. 21). However, resolution of corneal
opacification was noted after weeks 3 and 4 in the Del-
taRex-G (dnG1) vector-treated rabbits (FIG. 21 lower left
panel), as indicated by objective corneal haze assessment
scores. In contrast, rabbits treated with the control null
vector (FIG. 21 right panels) and the aG1 vector (FIG. 21
middle panels) showed sustained and progressive develop-
ment of corneal haze throughout the entire observation
period, which was statistically significant by multiple-com-
parisons t-test. The DeltaRex-G (dnG1) group showed less
corneal haze (arrows) than the aG1 and null control groups.

Example 15—Testing Efficacy of DeltaRex-G Therapy for COVID-19 in Humans

Subjects that are confirmed COVID-19 positive by viral
RT PCR and exhibiting pyrexia, elevated respiratory rate,
and cough are selected for treatment with a targeted ret-
rovector (DeltaRex-G).

DeltaRex-G is supplied as a sterile straw-colored liquid in
a 250 ml cryobag containing 60 ml vector/bag and stored
frozen at minus 75±10° C. Fifteen minutes before infusion,
the product is thawed in a 34° C. water bath and infused
within one hour upon thawing. The DeltaRex-G is admin-
istered via intravenous infusion at 4 ml/min through a
central or peripheral intravenous line up to a total volume of
200 ml/24 hours for seven days.

Daily and follow-up monitoring show an improvement of
clinical symptoms (including time to resolution of fever,
improvement in respiratory rate and $SpO_2$), a shorter length
of hospital stay, less need for mechanical ventilator therapy
and/or intensive care, and changes in cytokine pattern as
compared to similarly affected control subjects.

Example 16—Evaluating Efficacy of DeltaRex-G in Improving Survival and Hastening Recovery from Severe COVID-19 in Humans A subject presenting with acute hypoxic respiratory fail-
ure from severe COVID-19-related ARDS (i.e. exhibiting a $PaO_2/FiO_2$ of less than 100) and not responding to standard
of care therapy per NIH treatment guidelines for Severe
COVID-19 is assessed for clinical status, hematologic and
organ function, EKG, and chest xray/CT at baseline and as
needed throughout the course of treatment. The subject
receives DeltaRex-G intravenously a dose of $1.2\times10^{11}$ cfu
daily for seven days. All serious DeltaRex-G therapy related
or unexpected adverse events, all grade III or IV toxicities,
and autopsy reports if conducted in any death events are
reported.

For efficacy analysis, treatment outcome parameters
based on NCT04292899 Odds of Ratio for Improvement on
a 7-point Ordinal Scale are assessed on Day 14. The odds
ratio represents the odds of improvement in the ordinal
scale. The ordinal scale is an assessment of the clinical status
at a given day. Each day, the worst score from the previous
day is recorded. The scale is as follows: 1. Death; 2.
Hospitalized, on invasive mechanical ventilation or Extra-
corporeal Membrane Oxygenation (ECMO); 3. Hospital-
ized, on non-invasive ventilation or high flow oxygen
devices; 4. Hospitalized, requiring low flow supplemental
oxygen; 5. Hospitalized, not requiring supplemental oxy-
gen—requiring ongoing medical care (coronavirus related
or otherwise); 6. Hospitalized, not requiring supplemental
oxygen—no longer requiring ongoing medical care (other
than per protocol DeltaRex-G administration; 7. Not hospi-
talized.

It will be apparent to those having skill in the art that
many changes may be made to the details of the above-
described embodiments without departing from the under-
lying principles of the invention. The scope of the present
invention should, therefore, be determined only by the
following claims.

The invention claimed is:

1. A method of lessening a complication from coronavirus
disease 2019 (COVID-19) infection in a subject, wherein the
complication is selected from the group consisting of cyto-
kine release syndrome (CRS), acute respiratory distress
syndrome (ARDS), kidney damage, and liver damage, com-
prising administering to the subject a dose of a murine
leukemia virus (MLV)-based retroviral vector comprising a
collagen-binding motif and encoding an N-terminal deletion
mutant human cyclin G1 (CCNG1) construct, effective to
reduce severity of the complication.

* * * * *